(12) United States Patent
Nouchi et al.

(10) Patent No.: US 8,403,482 B2
(45) Date of Patent: Mar. 26, 2013

(54) FUNDUS OCULI OBSERVATION DEVICE AND PROGRAM CONTROLLING THE SAME

(75) Inventors: Takeyoshi Nouchi, Tokyo (JP); Kazuhiko Yumikake, Tokyo (JP); Hitoshi Shimizu, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 463 days.

(21) Appl. No.: 12/451,673

(22) PCT Filed: May 15, 2008

(86) PCT No.: PCT/JP2008/001212
§ 371 (c)(1),
(2), (4) Date: Mar. 4, 2010

(87) PCT Pub. No.: WO2008/146457
PCT Pub. Date: Dec. 4, 2008

(65) Prior Publication Data
US 2010/0182567 A1      Jul. 22, 2010

(30) Foreign Application Priority Data
May 24, 2007   (JP) .................................. 2007-137773

(51) Int. Cl.
*A61B 3/00* (2006.01)
*A61B 3/14* (2006.01)
*A61B 3/10* (2006.01)

(52) U.S. Cl. .......................... 351/208; 351/206; 351/221

(58) Field of Classification Search .................. 351/208, 351/200, 205–206, 210–211, 221, 246
See application file for complete search history.

(56) References Cited

U.S. PATENT DOCUMENTS

| 5,975,697 A * | 11/1999 | Podoleanu et al. | 351/206 |
| 2005/0140982 A1 | 6/2005 | Chen et al. | |
| 2006/0171503 A1 | 8/2006 | O'Hara et al. | |
| 2006/0244972 A1* | 11/2006 | Fercher | 356/497 |
| 2008/0030680 A1* | 2/2008 | Tsukada et al. | 351/206 |
| 2008/0285043 A1* | 11/2008 | Fercher et al. | 356/451 |
| 2010/0007848 A1* | 1/2010 | Murata | 351/206 |

FOREIGN PATENT DOCUMENTS

| EP | 1872713 A1 | 1/2008 |
| JP | 11-325849 A | 11/1999 |
| JP | 2002-139421 A | 5/2002 |
| JP | 2003-000543 A | 1/2003 |
| JP | 2007-117714 A | 5/2007 |
| WO | WO-2005/117534 A2 | 12/2005 |

OTHER PUBLICATIONS

T. Funaba, "Optical Coherence Tomography using Optical Frequency Domain Interference," Yamagatakenritsu Sangyo Tanki Daigakuko Kiyo, 2006, 12, pp. 73-78.

(Continued)

*Primary Examiner* — Dawayne A Pinkney
(74) *Attorney, Agent, or Firm* — Edwards Wildman Palmer LLP

(57) ABSTRACT

[Task] To provide a fundus oculi observation device capable of effectively performing dispersion compensation.
[Means for Resolution] A fundus oculi observation device 1 functions as an optical image measurement device that splits a broadband light into a signal light LS and a reference light LR, superimposes the signal light LS propagated through a fundus oculi Ef and the reference light LR propagated through a reference mirror 174 to generate an interference light LC and forms an image of the fundus oculi Ef. The device 1 corrects the influence of dispersion of the reference light LR based on ocular information 212a, generates the interference light LC after the correction, detects this interference light LC, and forms an OCT image.

16 Claims, 12 Drawing Sheets

OTHER PUBLICATIONS

International Search Report mailed Aug. 5, 2008, issued on PCT/JP2008/001212.

Supplementary European Search Report for European Patent Application No. 08751730,6 dated Jan. 12, 2011.

* cited by examiner

FUNDUS OCULI OBSERVATION DEVICE AND PROGRAM CONTROLLING THE SAME

TECHNICAL FIELD

The present invention relates to a fundus oculi observation device for observing the fundus oculi and a program controlling the device.

BACKGROUND ART

In recent years, attention has been focused on an optical image measurement technique of forming an image representing the surface morphology or internal morphology of a measurement object by using a light beam emitted from a laser light source or the like. Because this optical image measurement technique does not have invasiveness to human bodies unlike an X-ray CT device, it is expected to apply this technique particularly in the medical field.

Patent Document 1 discloses an optical image measurement device configured in a manner that: a measuring arm scans an object by using a rotary deflection mirror (Galvano mirror); a reference mirror is disposed to a reference arm; at the outlet thereof, such an interferometer is used that the intensity of a light appearing due to interference of light fluxes from the measuring arm and the reference arm is analyzed by a spectrometer; and the reference arm is provided with a device gradually changing the light flux phase of the reference light in non-continuous values.

The optical image measurement device disclosed in Patent Document 1 uses a method of so-called "Fourier Domain OCT (Optical Coherence Tomography)." That is to say, the morphology of a measurement object in the depth direction (z-direction) is imaged by applying a beam of a low-coherence light to the measurement object, acquiring the spectrum intensity distribution of the reflected light, and subjecting the acquired distribution to Fourier transform.

Furthermore, the optical image measurement device described in Patent Document 1 is provided with a Galvano mirror that scans with a light beam (a signal light), thereby being capable of forming an image of a desired measurement target region of a measurement object. Because this optical image measurement device scans with the light beam only in one direction (x-direction) orthogonal to the z-direction, a formed image is a two-dimensional tomographic image in the depth direction (z-direction) along the scanning direction (the x-direction) of the light beam.

Further, Patent Document 2 discloses a technique of scanning with a signal light in both the horizontal and vertical directions to thereby form a plurality of two-dimensional tomographic images in the horizontal direction and, based on the plurality of tomographic images, acquiring and imaging three-dimensional tomographic information of a measurement range. A method for three-dimensional imaging is, for example, a method of arranging and displaying a plurality of tomographic images in the vertical direction (referred to as stack data or the like), and a method of forming a three-dimensional image by subjecting a plurality of tomographic images to a rendering process.

Further, Patent Document 3 discloses a configuration of using such an optical image measurement device in the ophthalmic field.

[Patent Document 1] Japanese Unexamined Patent Application Publication No. 11-325849

[Patent Document 2] Japanese Unexamined Patent Application Publication No. 2002-139421

[Patent Document 3] Japanese Unexamined Patent Application Publication No. 2003-543

DISCLOSURE OF THE INVENTION

Problem that the Invention is to Solve

In a case that a conventional optical image measurement device is used for an observation of the fundus oculi, there is a problem as described below. To be specific, since there are various minute tissues in the fundus oculi, a highly accurate image is required for a favorable observation of the fundus oculi. For this purpose, it is desirable to reduce or remove the influence of light dispersion (called "dispersion compensation"). However, it is difficult to effectively perform dispersion compensation in a conventional device.

In particular, when considering the influence of dispersion caused by an ocular optical system, it is desirable to accurately perform dispersion compensation for an eye. However, in a conventional device, it is impossible to perform dispersion compensation for an eye.

In an optical image measurement, it is known that the width of the wavelength band of a light source corresponds to resolution in the depth direction of an image (depth resolution). In a case that a light source with a boarder wavelength band is applied to increase the depth resolution in a conventional device, the following problems may occur. To be specific, although interference positions of lights of the respective wavelengths should match essentially, the interference positions vary depending on the wavelengths due to the influence of dispersion, the interference positions spread as a whole, and the depth resolution deteriorates.

Further, since the influence of dispersion increases as the wavelength band of the light source is expanded, the accuracy of an image deteriorates.

The present invention was made to solve these problems, and an object of the present invention is to provide a fundus oculi observation device capable of effectively performing dispersion compensation, and a program that controls the device.

Means for Solving the Above Problem

In order to achieve the abovementioned object, in a first aspect of the present invention, a fundus oculi observation device that splits a broadband light into a signal light and a reference light, superimposes the signal light propagated through a fundus oculi and the reference light propagated through a reference object to generate an interference light, and forms an image of the fundus oculi based on a result of detection of the interference light, comprises: a storage configured to store ocular information including axial length information; and a corrector configured to correct an influence of dispersion exerted on the signal light and/or the reference light, based on the ocular information, and is characterized in that an interference light based on the broadband light is generated after the correction, the inference light is detected, and an image of the fundus oculi of the eye is formed based on a result of the detection.

Further, in a second aspect of the present invention, the fundus oculi observation device according to the first aspect is characterized in that the corrector includes a changing part configured to change a light path length of each wavelength component of the signal light and/or a light path length of each wavelength component of the reference light, and a controller configured to control the changing part based on the ocular information.

Further, in a third aspect of the present invention, the fundus oculi observation device according to the second aspect is characterized in that: the changing part includes a plurality of prisms, and a drive mechanism configured to move each of the plurality of prisms; and a controller is configured to control the drive mechanism based on the ocular information to change a position of each of the plurality of prisms on a light path of the signal light and/or on a light path of the reference light.

Further, in a fourth aspect of the present invention, the fundus oculi observation device according to the second aspect is characterized in that: the changing part includes a liquid cell in which a liquid is sealed, and a change mechanism configured to change an amount of the liquid sealed in the liquid cell; and the controller is configured to control the liquid amount change mechanism based on the ocular information to change a crossover distance between a light path of the signal light and/or a light path of the reference light and the liquid cell.

Further, in a fifth aspect of the present invention, the fundus oculi observation device according to the first aspect is characterized in that the corrector is configured to obtain an equation between a light path length of the signal light and a light path length of the reference light based on the ocular information, and to correct the influence of dispersion based on the equation.

Further, in a sixth aspect of the present invention, the fundus oculi observation device according to the fifth aspect is characterized in that: the ocular information includes refraction index information of an ocular optical system; and the corrector is configured to calculate the light path length of the signal light based on the axial length information, the refraction index information and a light path length from a split position of the broadband light to the eye, and to obtain an equation of the calculated light path length of the signal light and the light path length of the reference light, as the equation.

Further, in a seventh aspect of the present invention, the fundus oculi observation device according to the sixth aspect is characterized in that the corrector is configured to calculate an optical distance of the ocular optical system based on the axial length information and the refraction index information, to obtain, as the equation, an equation that relates the light path length from the split position to the eye, the light path length of the reference light, the optical distance of the ocular optical system, and an unknown correction distance, for each of a plurality of wavelength components of the broadband light, to calculate the correction distance based on the equation, and to correct the influence of dispersion based on a result of the calculation.

Further, in an eighth aspect of the present invention, the fundus oculi observation device according to the sixth aspect further comprises an alignment part for performing alignment of a device optical system with the eye, and is characterized in that the corrector is configured to calculate the light path length from the split position to the eye based on a result of the alignment.

Further, in a ninth aspect of the present invention, the fundus oculi observation device according to the eighth aspect is characterized in that the corrector includes a detector configured to detect an error of the alignment, and is configured to obtain the relation expression by reflecting the error.

Further, in a tenth aspect of the present invention, the fundus oculi observation device according to the fifth aspect is characterized in that the corrector is configured to obtain the light path length of the reference light based on a light path length from a split position of the broadband light to the reference object.

Further, in an eleventh aspect of the present invention, the fundus oculi observation device according to the fifth aspect is characterized in that the corrector includes a changing part configured to change a light path length for each wavelength component of the signal light and/or a light path length for each wavelength component of the reference light, and a controller configured to control the changing part based on the equation.

Further, in a twelfth aspect of the present invention, the fundus oculi observation device according to the first aspect further comprises a measurement part configured to measure an axial length of the eye, and is characterized in that the storage is configured to store a result of the measurement as the axial length information.

Further, in a thirteenth aspect of the present invention, the fundus oculi observation device according to the first aspect is characterized in that the corrector is configured to, after correcting the influence of dispersion based on the ocular information, further correct the influence of dispersion so as to decrease a depth resolution of the image of the fundus oculi based on a signal as the result of the detection of the interference light.

Further, in a fourteenth aspect of the present invention, a fundus oculi observation device that splits a broadband light into a signal light and a reference light, superimposes the signal light propagated through a fundus oculi and the reference light propagated through a reference object to generate an interference light, and forms an image of the fundus oculi based on a result of detection of the interference light, comprises: a corrector configured to correct an influence of dispersion so as to decrease a depth resolution of the image of the fundus oculi, based on a signal as a result of detection of the interference light, and is characterized in that an interference light based on the broadband light is generated after the correction, the inference light is detected, and an image of the fundus oculi of the eye is formed based on a result of the detection.

Further, in a fifteenth aspect of the present invention, the fundus oculi observation device according to the thirteenth or fourteenth aspect is characterized in that the corrector is configured to correct the influence of dispersion so as to widen a width of an envelope curve of the signal.

Further, in a sixteenth aspect of the present invention, the fundus oculi observation device according to the thirteenth or fourteenth aspect is characterized in that the corrector is configured to correct the influence of dispersion so as to decrease a half width of a signal obtained by Fourier transform of the signal.

Further, in a seventeenth aspect of the present invention, a program that controls a fundus oculi observation device that includes a computer, splits a broadband light into a signal light and a reference light, superimposes the signal light propagated through a fundus oculi and the reference light propagated through a reference object to generate an interference light, and forms an image of the fundus oculi based on a result of detection of the interference light, is characterized in that: the computer is caused to store ocular information including axial length information and correct an influence of dispersion exerted on the signal light and/or the reference light based on the axial length information; and the fundus oculi observation device, after the correction, generates an interference light based on the broadband light, detects the interference light, and forms an image of the fundus oculi of the eye based on a result of the detection.

Further, in an eighteenth aspect of the present invention, a program that controls a fundus oculi observation device that includes a computer, splits a broadband light into a signal light and a reference light, superimposes the signal light propagated through a fundus oculi and the reference light propagated through a reference object to generate an interference light, and forms an image of the fundus oculi based on a result of detection of the interference light, is characterized in that: the computer is caused to correct the influence of dispersion so as to decrease a depth resolution of the image of the fundus oculi, based on a signal as the result of the detection of the interference light; and the fundus oculi observation device, after the correction, generates an interference light based on the broadband light, detects the interference light, and forms an image of the fundus oculi of the eye based on a result of the detection.

Effect of the Invention

According to the present invention, since it is possible to correct the influence of dispersion of a signal light and/or a reference light based on ocular information and form a fundus oculi image of an eye based on the result of detection of an interference light generated after the correction, it is possible to perform effective dispersion compensation considering the influence of dispersion caused by an ocular optical system.

Further, according to the present invention, since it is possible to correct the influence of dispersion so that the depth resolution of an image is minimized based on the result of detection of an interference light and form a fundus oculi image of an eye based on the result of detection of an interference light generated after the correction, it is possible to effectively perform dispersion compensation.

BRIEF DESCRIPTION OF THE DRAWINGS

FIG. 9A shows an example of the scanning pattern of the signal light when the fundus oculi is seen from the incident side of the signal light into an eye. FIG. 9B shows an example of an arrangement pattern of scanning points on each scanning line.

Figure 1:
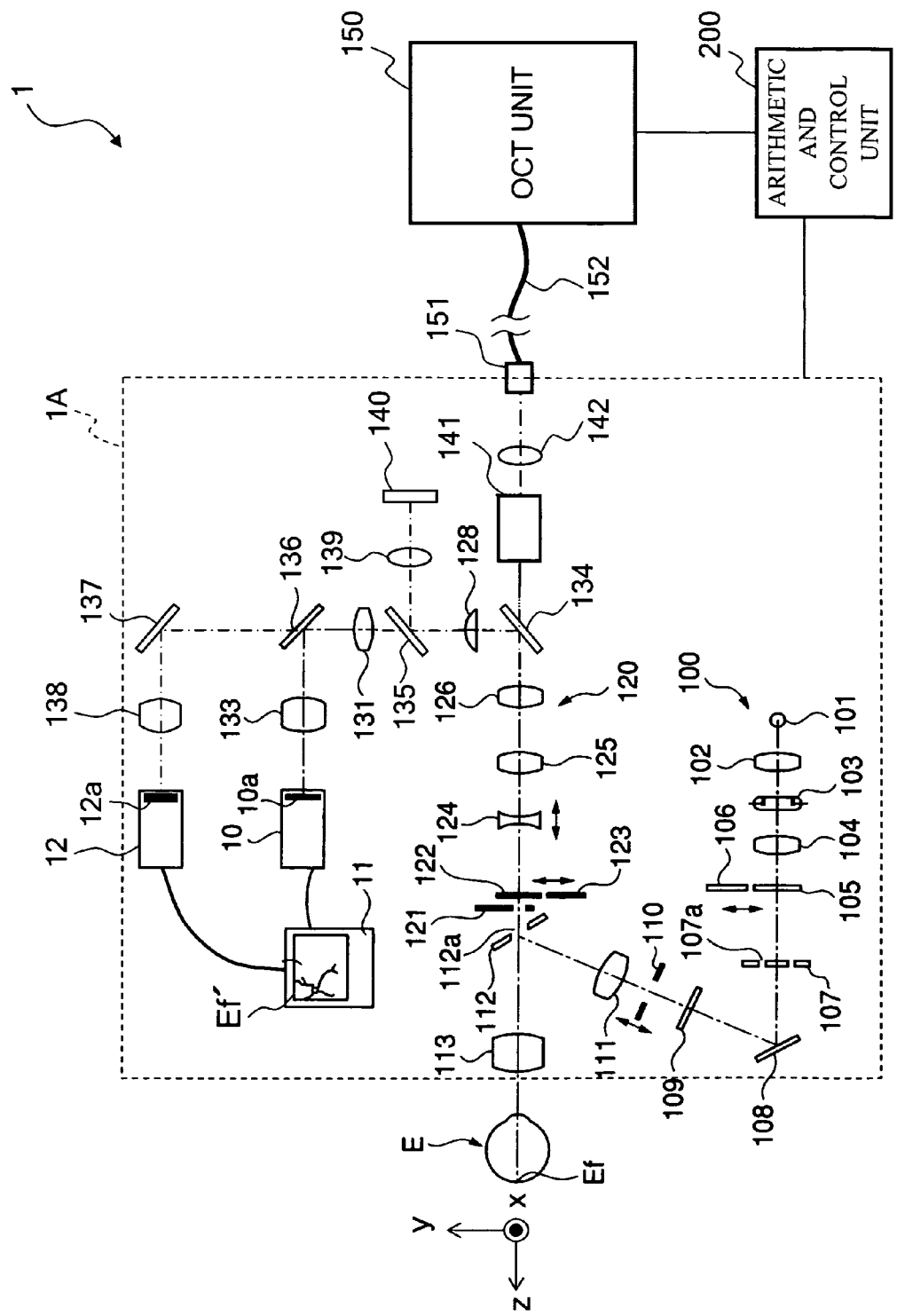
FIG. 1 is a schematic configuration diagram showing an example of the entire configuration in a preferred embodiment of a fundus oculi observation device according to the present invention.

DESCRIPTION OF REFERENCE NUMERALS
AND SYMBOLS

1 fundus oculi observation device
1A retinal camera unit
150 OCT unit
160 low-coherence light source
162 optical coupler
174 reference mirror
175 pair prism
180 spectrometer
184 CCD
190A alignment optical system
200 arithmetic and control unit
204*a* control program
210 controller
211 main controller
212 storage
212*a* ocular information
213 calculation processor
213*a* axial length calculator
213*b* error calculator
213*c* correction amount calculator
220 image forming part
230 image processor
240 user interface
240A display
240B manipulation part
243 reference mirror drive mechanism
244 prism drive mechanism
E eye
Ef fundus oculi

BEST MODE FOR CARRYING OUT THE
INVENTION

An example of an embodiment of a fundus oculi observation device and a program that controls the device according to the present invention will be described in detail with reference to the drawings. Below, dispersion compensation in the present embodiment will be first described, and then the fundus oculi observation device and the program will be described.

[Dispersion Compensation]

Dispersion is a phenomenon occurring because a light speed in a medium differs depending on wavelengths. In a medium other than a vacuum state, specific dispersion exists. However, since the influence of dispersion in the air is small, it is usually ignored.

Figure 12:
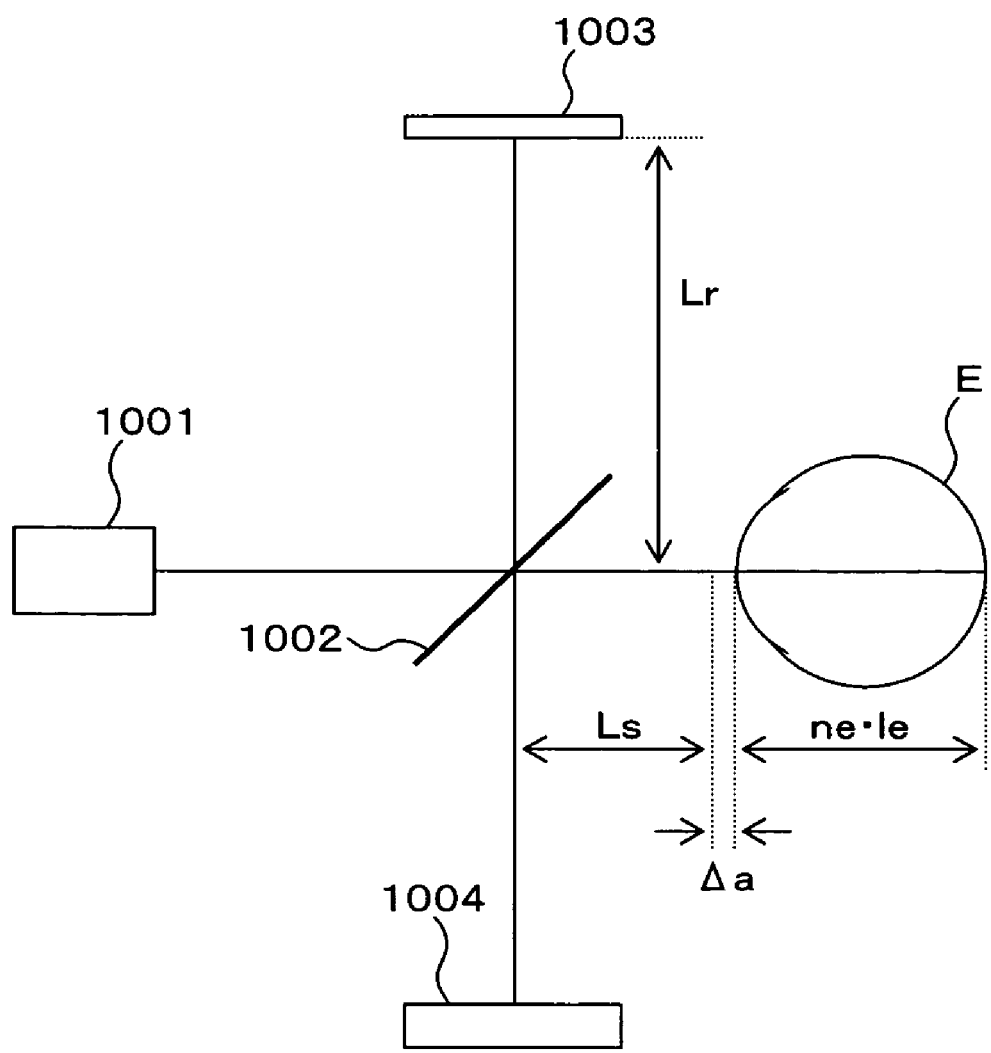
FIG. 12 is a schematic explanation diagram for explaining dispersion compensation by the fundus oculi observation device and the program according to the invention.

Dispersion compensation in a fundus oculi observation device capable of acquiring an OCT image will be described with reference to FIG. 12. FIG. 12 schematically shows a configuration for acquiring an OCT image of the fundus oculi (an optical image measurement device). In practice, optical elements such as various lenses, a computer, and so on are installed, but they are omitted to simplify the description.

The optical image measurement device shown in FIG. 12 has a light source 1001, a beam splitter 1002, a reference mirror 1003 and a detector 1004, and configures a Michelson-type interferometer. Although a description here will be made for use of a Michelson-type interferometer, which is the most common, it is similar for other types of interferometers.

Before a measurement, alignment of a device optical system with an eye E is performed. Consequently, the light path length of a signal light described below is determined, and the light path length of a corresponding reference light is also determined.

A broadband light emitted from the light source 1001 is split into halves by the beam splitter 1002. A light travelling toward the eye E will be referred to as a signal light and a light travelling toward the reference mirror 1003 will be referred to as a reference light.

The signal light is reflected by the fundus oculi of the eye E and returned to the beam splitter 1002. On the other hand, the reference light is reflected by the reference mirror 1003 and returned to the beam splitter 1002. The signal light and the reference light are superimposed by the beam splitter 1002, and an interference light is thereby generated.

The interference light is detected by the detector 1004. A computer, which is not shown, forms an OCT image such as a tomographic image of the fundus oculi based on the result of the detection.

In this case, there is a relation as shown below between the light path length of the signal light (a signal light path length: right hand side) and the light path length of the reference light (a reference light path length: left hand side).

[Equation 1]

$$Lr = Ls + \Delta a + ne \cdot le \quad (1)$$

Here, Lr on the left hand side represents the reference light path length. Ls on the right hand side represents an optical distance between the beam splitter 1002 (a split position of the broadband light) and the eye E.

Further, $\Delta a$ represents an alignment error. The alignment error can be detected as described below. When the alignment error is not considered, the above equation without this term can be used (this is similar below).

Further, ne represents the refraction index of the ocular optical system, and le represents the axial length of the eye E. The axial length may be a measurement value of the axial length of the eye E, a value of an eyeball model such as a Gullstrand model eye, or a clinically obtained statistical value (such as an average value).

Moreover, the refraction index may be a measurement value of the eye E, or may be a clinically obtained statistical value. There are sites having different refraction indexes such as the cornea, lens and vitreous in the eyeball, and it is desirable to perform calculation by using the refraction indexes of these sites individually. However, it will be simplified and described here.

Further, the light path length is not a spatial distance but an optical distance considering the refraction index, thickness and so on of the optical elements. Although the optical elements on the light path are omitted in FIG. 12, the actual signal light path length and reference light path length are optical distances considering the influence of these optical elements. The refraction index of the air on the light path may be or may not be considered.

In order to reflect the influence of dispersion, a plurality of (in this case, two) wavelengths of the broadband light are considered. In this case, it is possible to use, for example, a wavelength on the short-wavelength side and a wavelength on the long-wavelength side of a half width of the band of the broadband light.

Assuming that dispersion compensation is performed considering the light path length ne·le of the eye E, in addition to the above equation (1), the following two equations (2) and (3) are established.

[Equation 2]

$$Lr1 = Ls1 + \Delta a + ne1 \cdot le \quad (2)$$

[Equation 3]

$$Lr2 = Ls2 + \Delta a + ne2 \cdot le \quad (3)$$

Here, Lr1 represents a light path length of a wavelength component on the short-wavelength side of the reference light (short-wavelength component). Ls1 represents a light path length of a short-wavelength component of the signal light between the beam splitter 1002 and the eye E. ne1 represents a refraction index of the ocular optical system with respect to the light of the wavelength on the short-wavelength side.

Further, Lr2 represents a light path length of a wavelength component on long-wavelength side of the reference light (long-wavelength component). Ls2 represents a light path length of a long wavelength component of the signal light between the beam splitter 1002 and the eye E. ne2 represents a refraction index of the ocular optical system with respect to the light of the wavelength on the long-wavelength side.

A resolution $\Delta z$ in the depth direction in the optical image measurement will be considered. As known, the depth resolution $\Delta z$ is derived from the following equation.

[Equation 4]

$$\Delta z = 2 \ln 2/\pi \cdot \lambda_0^2 / \Delta \lambda \quad (4)$$

Here, $\lambda_0$ represents a center wavelength of the broadband light, and $\Delta \lambda$ represents a half width. As shown in Equation (4), the center wavelength $\lambda_0$ and the half width $\Delta \lambda$ are variables in order to increase the accuracy of an image, but it is difficult to change the center wavelength $\lambda_0$ because the center wavelength $\lambda_0$ is limited by not only a light source to be used but also an influence on the eye E. Therefore, in order to decrease the depth resolution $\Delta z$, it is necessary to increase the half width $\Delta \lambda$.

In a case that the half width $\Delta \lambda$ is increased without execution of dispersion compensation, the influence of dispersion increases, which causes spread of the interference positions of lights as mentioned above and leads to deterioration of the image quality. Therefore, in the case of increasing the half width $\Delta \lambda$ to increase the depth resolution $\Delta z$, it is required to perform dispersion compensation with high accuracy.

Under such a background, dispersion compensation in a case that the axial length is longer than le by $\Delta$le will be considered. Dispersion compensation in such a case that the axial length is shorter can be considered in a like manner.

An dispersion compensation optical element is placed on the light path of the reference light. This optical element adds an optical distance Ld to the reference light path length Lr. By implementing such dispersion compensation, the following three equations (5), (6) and (7) are established. In the respective equations (5) to (7), the left hand side represents the light path length of the reference light, whereas the right hand side represents the light path length of the signal light.

[Equation 5]

$$Lr+Ld=Ls+\Delta a+ne\cdot(le+\Delta le) \quad (5)$$

[Equation 6]

$$Lr1+Ld1=Ls1+\Delta a+ne1\cdot(le+\Delta le) \quad (6)$$

[Equation 7]

$$Lr2+Ld2=Ls2+\Delta a+ne2\cdot(le+\Delta le) \quad (7)$$

Here, Ld1 represents an optical distance added to the light path length Lr1 of the short-wavelength component of the reference light by the dispersion compensation optical element. Moreover, Ld2 represents an optical distance added to the light path length Lr2 of the long-wavelength component of the reference light by the dispersion compensation optical element.

When there is a difference in dispersion amount in a medium between the eye E and the dispersion compensation optical element, that is, when there is a difference in light path length between the short-wavelength component and the long-wavelength component, dispersion compensation can be performed so as to correct (cancel) the dispersion amount. A difference in light path length of the center wavelength component caused thereby can be corrected by an interval of the air (namely, a spatial distance) between the signal light side and the reference light side, when dispersion in the air is ignored.

In the embodiment described below, based on the equations (5)-(7), the values of Ld, Ld1 and Ld2 (correction distances) are obtained, and the correction amount is determined in the above manner to perform dispersion compensation.

In the above description, dispersion of the reference light is corrected by using the equations (5)-(7), but it is also possible to correct dispersion of the signal light by using similar equations. Alternatively, dispersion compensation may be performed by correcting both the reference light and the signal light.

Further, in the above description, a wavelength component of a half width is used, but it is also possible to perform dispersion compensation by using other wavelength components. In particular, it is desirable to decrease the difference in light path length of many wavelength components over the entire wavelength band of the broadband light, and furthermore, it is desirable to perform dispersion compensation so as to minimize the difference in light path length of all the wavelength components of the broadband light.

Further, as the standard value le of the axial length, it is possible to appropriately use the value of an eyeball model, a clinically obtained statistical value, an actual measurement value of the eye E and so on as mentioned above. The displacement of the reference mirror 1003 from a position corresponding to the standard value le is equivalent to the variation amount Δle of the axial length mentioned before.

The dispersion compensation according to the present invention is not limited to the method described above, and it is possible to perform the dispersion compensation by determining the correction amount by any method based on information on the ocular optical system.

[Configuration]

Figure 4:
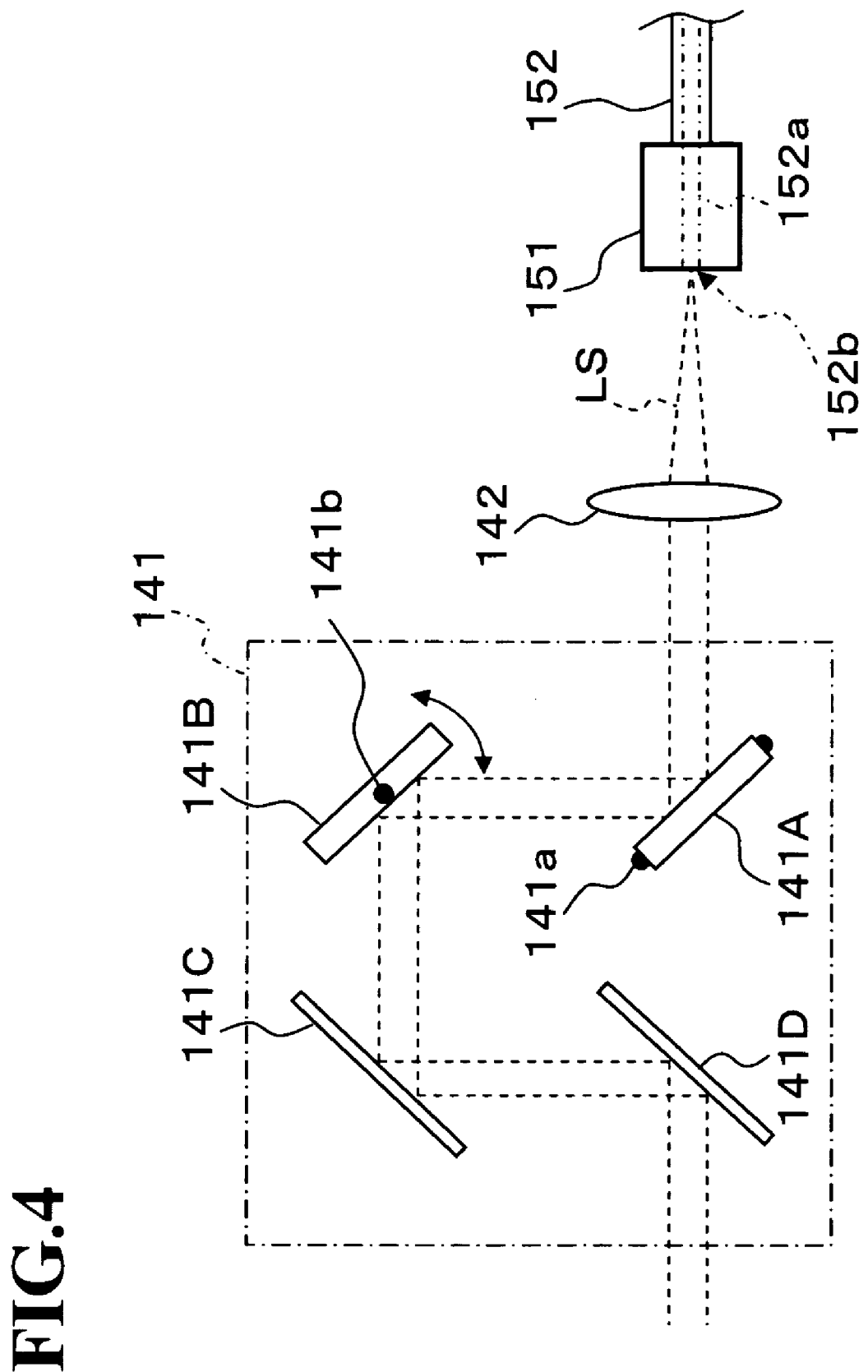
FIG. 4 is a schematic configuration diagram showing an example of the configuration of a scan unit installed in a retinal camera unit in the preferred embodiment of the fundus oculi observation device according to the present invention.
Figure 5:
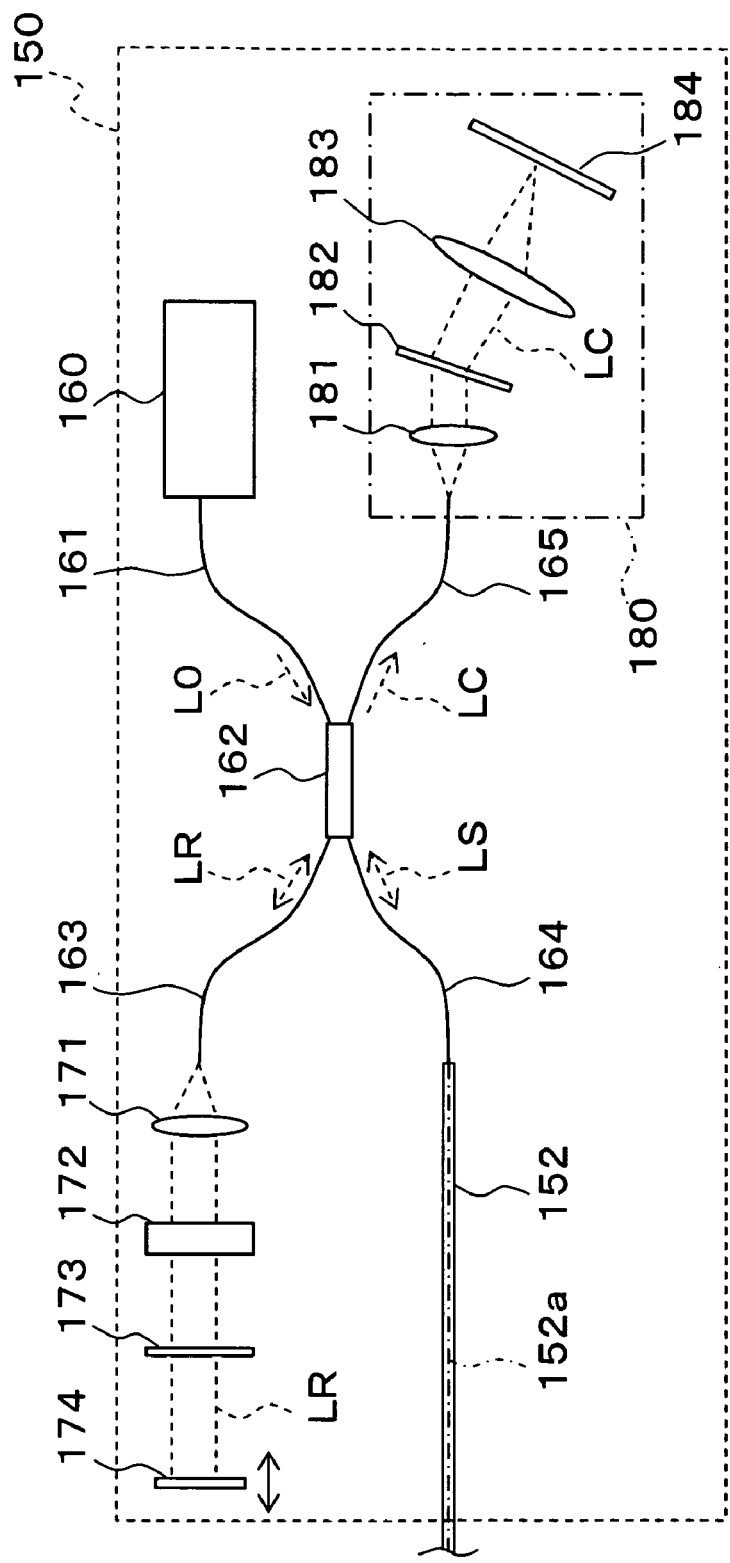
FIG. 5 is a schematic configuration diagram showing an example of the configuration of an OCT unit in the preferred embodiment of the fundus oculi observation device according to the present invention.
Figure 6:
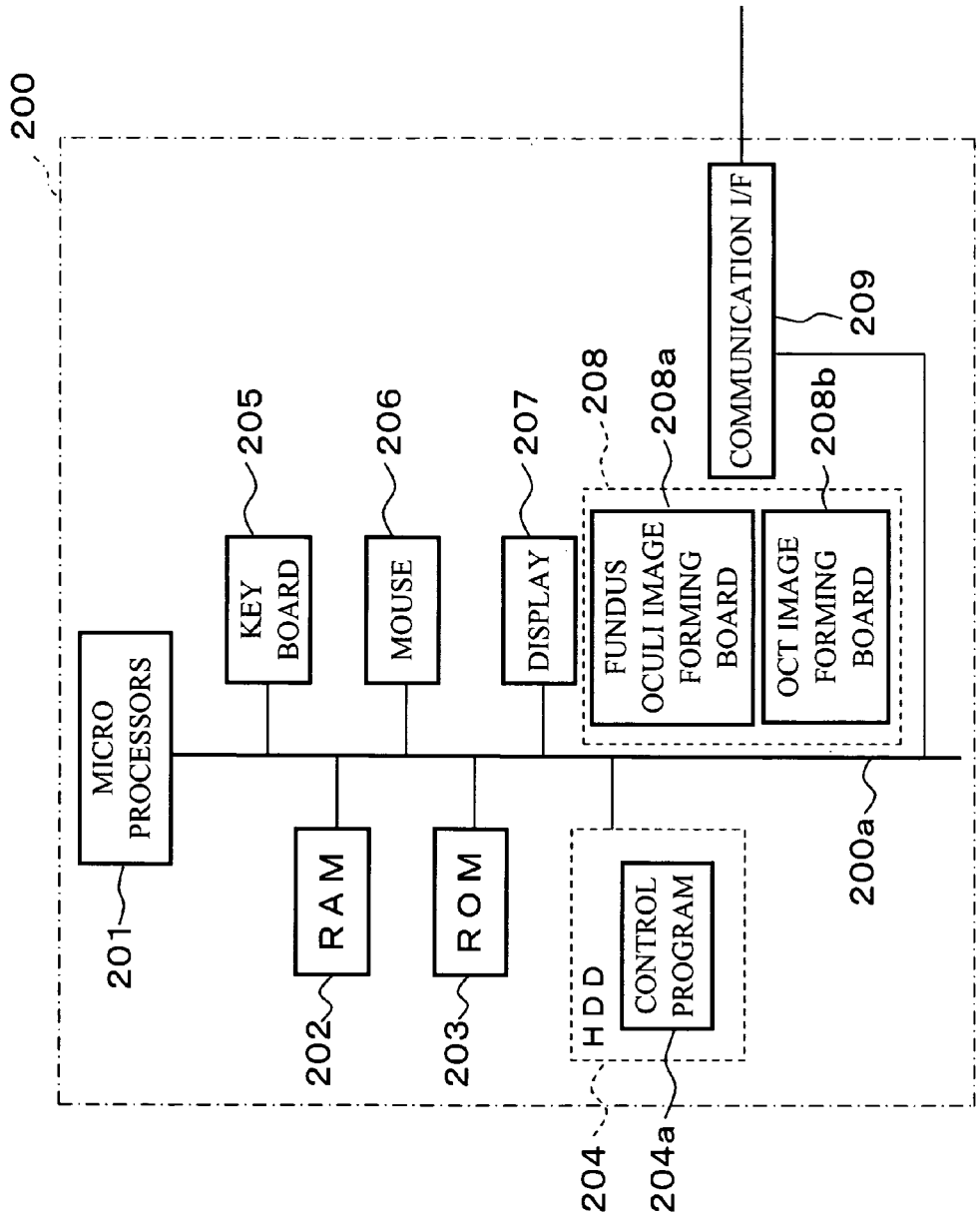
FIG. 6 is a schematic block diagram showing an example of the hardware configuration of an arithmetic and control unit in the preferred embodiment of the fundus oculi observation device according to the present invention.
Figure 7:
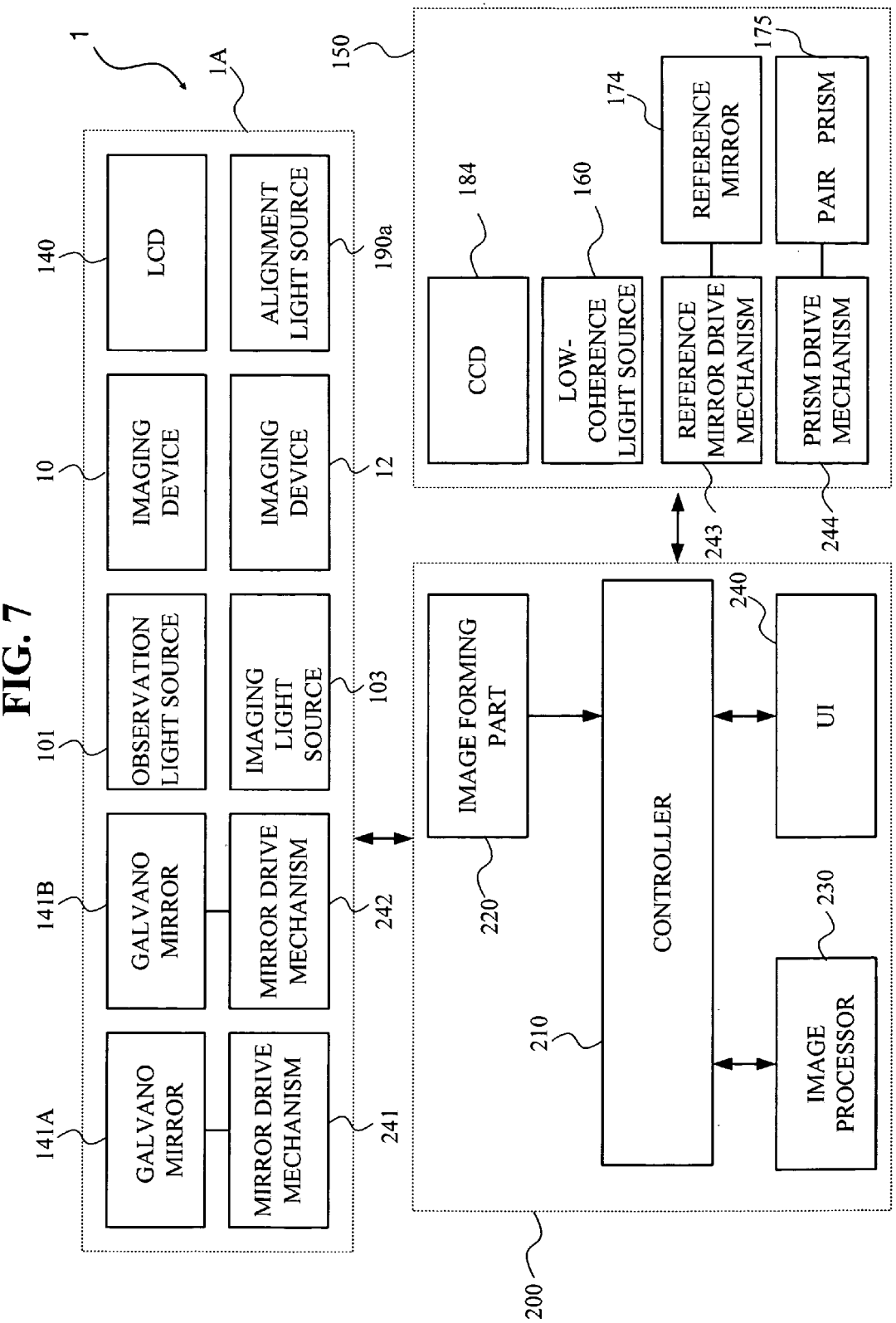
FIG. 7 is a schematic block diagram showing an example of the configuration of a control system in the preferred embodiment of the fundus oculi observation device according to the present invention.
Figure 8:
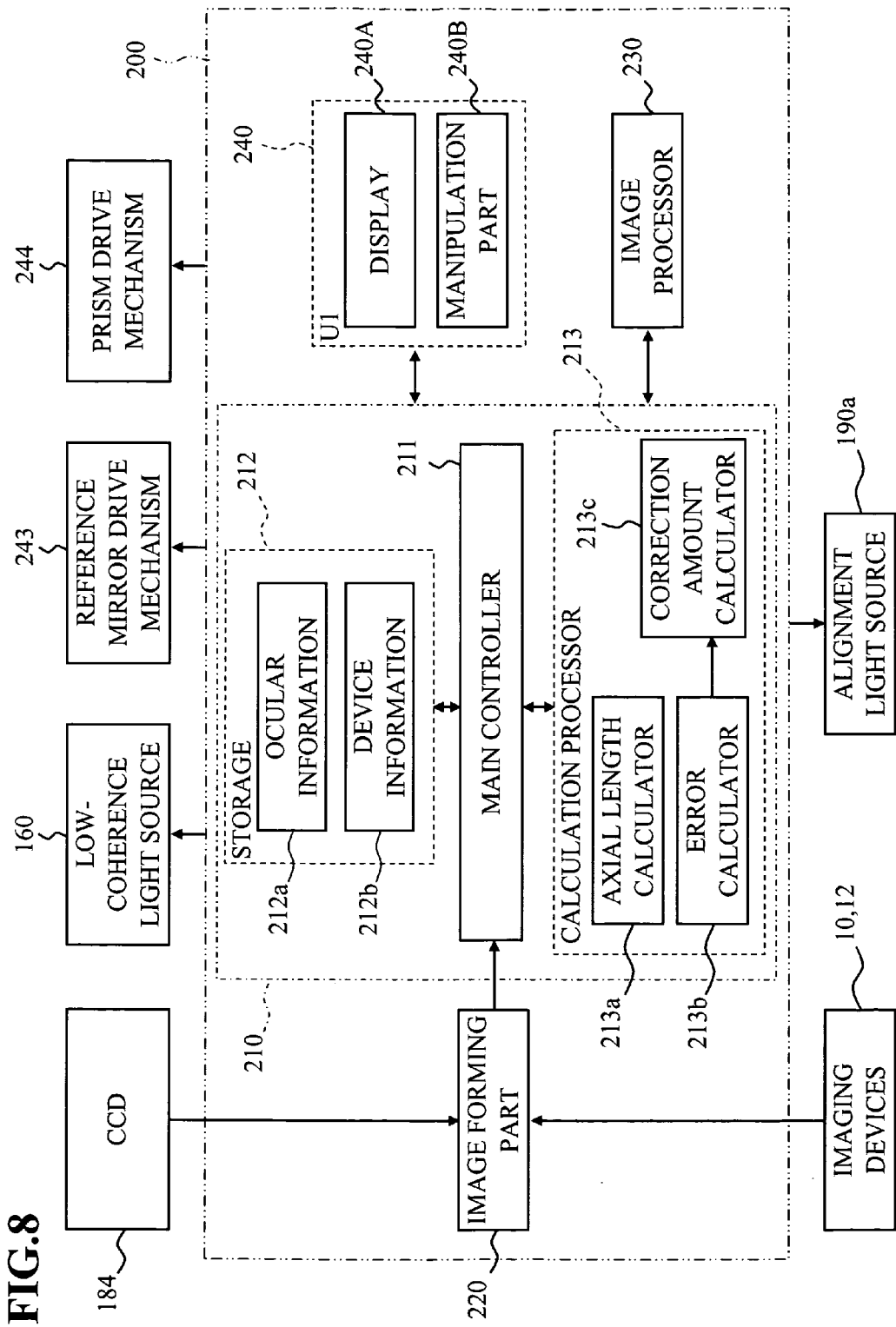
FIG. 8 is a schematic block diagram showing an example of the configuration in the embodiment of the fundus oculi observation device according to the present invention.

The configuration of the fundus oculi observation device according to the present embodiment will be explained with reference to FIGS. 1-8. FIG. 1 shows an example of the entire configuration of a fundus oculi observation device 1 according to the present embodiment. FIG. 2 shows an example of the configuration of an alignment optical system of the fundus oculi observation device 1. FIG. 3 shows an example of an alignment operation using this alignment optical system. FIG. 4 shows an example of the configuration of a scan unit 141 within a retinal camera unit 1A of the fundus oculi observation device 1. FIG. 5 shows an example of the configuration of an OCT unit 150 of the fundus oculi observation device 1. FIG. 6 shows an example of the hardware configuration of an arithmetic and control unit 200 of the fundus oculi observation device 1. FIG. 7 shows an example of a control system of the fundus oculi observation device 1. FIG. 8 shows an example of the configuration of the control system of the arithmetic and control unit 200.

[Entire Configuration]

As shown in FIG. 1, the fundus oculi observation device 1 includes the retinal camera unit 1A that functions like a conventional retinal camera, the OCT unit 150 that houses an optical system of the optical image measurement device (OCT device), and the arithmetic and control unit 200 that executes various arithmetic processes, control processes, or the like.

To the OCT unit 150, one end of a connection line 152 is attached. A connector part 151 is attached to the other end of the connection line 152. The connector part 151 is mounted on a mounting part 8c of the retinal camera unit 1A. Moreover, a conductive optical fiber runs through inside the connection line 152. The OCT unit 150 and the retinal camera unit 1A are optically connected via the connection line 152. The detailed configuration of the OCT unit 150 will be described later with reference to FIG. 5.

[Configuration of Retinal Camera Unit]

First, with reference to FIGS. 1-4, the retinal camera unit 1A will be described. The retinal camera unit 1A is a device that forms a two-dimensional image of the fundus oculi surface of an eye based on optically acquired data (data detected by imaging devices 10 and 12). Like a conventional retinal camera, the retinal camera unit 1A is provided with an illumination optical system 100 that illuminates a fundus oculi Ef of an eye E, and an imaging optical system 120 that guides the fundus oculi reflected light of the illumination light to the imaging device 10.

The imaging device 10 in the imaging optical system 120 of this embodiment detects an illumination light having a wavelength of near-infrared region, the details of which will be described later. Moreover, the imaging optical system 120 is also provided with the imaging device 12 that detects an illumination light having a wavelength of visible region. Moreover, the imaging optical system 120 guides a signal light inputted from the OCT unit 150 to the fundus oculi Ef and outputs the signal light propagated through the fundus oculi Ef to the OCT unit 150.

As conventional, the illumination optical system 100 includes an observation light source 101, a condenser lens 102, an imaging light source 103, a condenser lens 104, exciter filters 105 and 106, a ring transparent plate 107, a mirror 108, an LCD (Liquid Crystal Display) 109, an illumination diaphragm 110, a relay lens 111, an aperture mirror 112, and an objective lens 113.

The observation light source 101 outputs an illumination light having a wavelength of visible region included in a range of about 400-700 nm. On the other hand, the imaging light source 103 outputs an illumination light having a wavelength of near-infrared region included in a range of about 700-800 nm. The near-infrared light outputted from the imaging light source 103 is set so as to have a shorter wavelength than a light used by the OCT unit 150 (described later).

On the other hand, the imaging optical system 120 includes the objective lens 113, the (aperture 112a of the) aperture mirror 112, an imaging diaphragm 121, barrier filters 122 and 123, a focusing lens 124, a relay lens 125, an imaging lens 126, a dichroic mirror 134, a field lens 128, a half mirror 135, a relay lens 131, a dichroic mirror 136, an imaging lens 133, the imaging device 10 (an image pick-up element 10a), a reflection mirror 137, an imaging lens 138, the imaging device 12 (an image pick-up element 12a), a lens 139, and an LCD 140. These are similar components to those of a conventional retinal camera.

Furthermore, the imaging optical system 120 is provided with the dichroic mirror 134, the half mirror 135, the dichroic mirror 136, the reflection mirror 137, the imaging lens 138, the lens 139, and the LCD 140.

The dichroic mirror 134 is configured to reflect the fundus oculi reflected light (having a wavelength included in a range of about 400-800 nm) of the illumination light coming from the illumination optical system 100, and to transmit a signal light LS (having a wavelength included in a range of about 800-900 nm; described later) coming from the OCT unit 150.

The dichroic mirror 136 is configured to transmit the illumination light having a wavelength of visible region coming from the illumination optical system 100 (a visible light having a wavelength of about 400-700 nm outputted from the observation light source 101), and to reflect the illumination light having a wavelength of near-infrared region (a near-infrared light having a wavelength of about 700-800 nm outputted from the imaging light source 103).

The LCD 140 acts to display an internal fixation target or the like. The light outputted from a display screen of the LCD 140 is focused by the lens 139, reflected by the half mirror 135, propagated through the field lens 128, and reflected by the dichroic mirror 136. Then, this light is propagated through the imaging lens 126, the relay lens 125, the focusing lens 124, the (aperture 112a of the) aperture mirror 112, the objective lens 113 and so on, and enters the eye E. Consequently, an internal fixation target or the like is projected onto the fundus oculi Ef of the eye E.

The image pick-up element 10a is an image pick-up element such as a CCD or a CMOS installed in the imaging device 10 such as a TV camera, and is particularly used for detecting a light having a wavelength of near-infrared region (in other words, the imaging device 10 is an infrared TV camera having sensitivity to a light of near-infrared region). The imaging device 10 outputs video signals as the result of detection of the near-infrared light. A touch panel monitor 11 displays a two-dimensional image of the surface of the fundus oculi Ef (a fundus oculi image Ef') based on the video signals. The video signals are sent to the arithmetic and control unit 200, and the fundus oculi image is displayed on a display (described later). For imaging the fundus oculi by the imaging device 10, for example, an illumination light having a wavelength of near-infrared region outputted from the imaging light source 103 of the illumination optical system 100 is used.

On the other hand, the image pick-up element 12a is an image pick-up element such as a CCD or a CMOS installed in the imaging device 12 such as a TV camera, and particularly detects a light having a wavelength of visible region (in other words, the imaging device 12 is a TV camera that has sensitivity to a visible light). The imaging device 12 outputs video signals as the result of detection of the visible light. The touch panel monitor 11 displays a two-dimensional image of the surface of the fundus oculi Ef (the fundus oculi image Ef') based on the video signals. The video signals are sent to the arithmetic and control unit 200, and the fundus oculi image is displayed on the display (described later). For imaging the fundus oculi by the imaging device 12, for example, an illumination light having a wavelength of visible region outputted from the observation light source 101 of the illumination optical system 100 is used.

The imaging optical system 120 of this embodiment is provided with a scan unit 141 and a lens 142. The scan unit 141 is provided with a configuration of scanning the fundus oculi Ef with a light outputted from the OCT unit 150 (the signal light LS; described later).

The lens 142 collimates the signal light LS guided from the OCT unit 150 through the connection line 152, and makes the light enter the scan unit 141. Further, the lens 142 acts to focus the fundus oculi reflected light of the signal light LS propagated through the scan unit 141.

FIG. 4 shows an example of a specific configuration of the scan unit 141. The scan unit 141 includes Galvano mirrors 141A and 141B, and reflection mirrors 141C and 141D.

The Galvano mirrors 141A and 141B are configured to be rotatable about rotary shafts 141a and 141b, respectively. The rotary shafts 141a and 141b are arranged orthogonally to each other. In FIG. 4, the rotary shaft 141a of the Galvano mirror 141A is arranged in the parallel direction to the paper face of FIG. 4. On the other hand, the rotary shaft 141b of the Galvano mirror 141B is arranged in the orthogonal direction to the paper face of FIG. 4. That is to say, the Galvano mirror 141B is configured to be rotatable in the directions indicated by an arrow pointing in both directions in FIG. 4, whereas the Galvano mirror 141A is configured to be rotatable in the directions orthogonal to the arrow pointing in both the directions. Consequently, the pair of Galvano mirrors 141A and 141B act to change reflection directions of the signal light LS into directions orthogonal to each other, respectively. The rotation operation of each of the Galvano mirrors 141A and 141B is driven by mirror drive mechanisms described later (refer to FIG. 7).

The signal light LS reflected by the Galvano mirrors 141A and 141B is reflected by the reflection mirrors 141C and 141D, and travels in the same direction as having entered the Galvano mirror 141A.

The conductive optical fiber 152a runs through the inside of the connection line 152. An end face 152b of the optical fiber 152a is arranged facing the lens 142. The signal light LS emitted from the end face 152b travels expanding its beam diameter toward the lens 142, and is collimated by the lens 142. On the contrary, the signal light LS propagated through the fundus oculi Ef is focused to the end face 152b by the lens 142.

A half mirror 190 is inclined on a light path between the focusing lens 124 and the relay lens 125. The half mirror 190 acts to combine the light path of an alignment optical system 190A shown in FIG. 2A and the light path of the imaging optical system 120 (an imaging light path).

An alignment bright point is used for both alignment for matching the corneal apex of the eye E with the optical axes of the optical systems 100 and 120 (alignment in the xy-directions shown in FIG. 1) and alignment of a distance between the eye E and the optical systems 100 and 120 (the z-direction in FIG. 1; working distance; a distance between (the apex of) the cornea of the eye E and the objective lens 113) (refer to Japanese Unexamined Patent Application Publication JP-A 11-4808, for example).

Figure 2A:
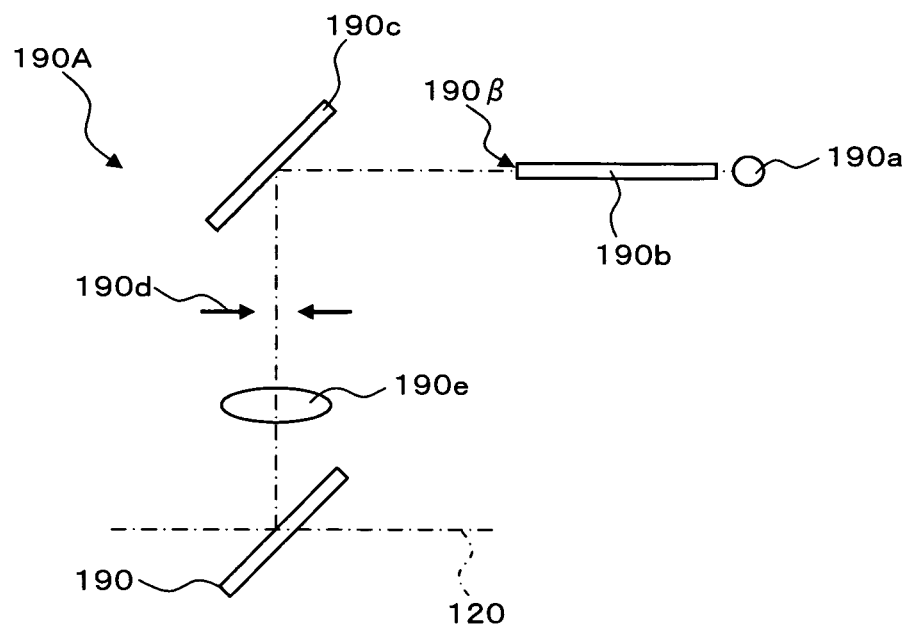
FIGS. 2A and 2B are schematic configuration diagrams showing an example of the configuration of an alignment optical system installed in a retinal camera unit in the preferred embodiment of the fundus oculi observation device according to the present invention.

As shown in FIG. 2A, the alignment optical system 190A includes the half mirror 190, and also includes an alignment light source 190a composed of, for example, an LED that emits a light such as a near-infrared light (an alignment light), a light guide 190b, a reflection mirror 190c, a two-hole aperture 190d, and a relay lens 190e.

Figure 2B:
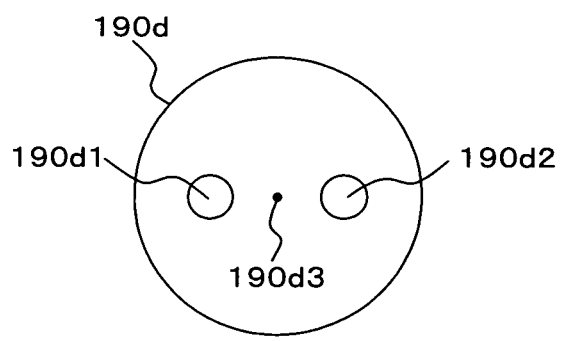

As shown in FIG. 2B, the two-hole aperture 190d has two holes 190d1 and 190d2. The holes 190d1 and 190d2 are formed, for example, at symmetric positions about a center position 190d3 of the disk-shaped two-hole aperture 190d. The two-hole aperture 190d is arranged so that the center position 190d3 is located on the optical axis of the alignment optical system 190A.

The alignment light emitted from an emission end 190β of the light guide 190b is reflected by the reflection mirror 190c and guided to the two-hole aperture 190d. (Part of) the alignment light passed through the holes 190d1 and 190d2 of the two-hole aperture 190d are propagated through the relay lens 190e, reflected by the half mirror 190, and guided to the aperture mirror 112. At this moment, the relay lens 190e performs intermediate image forming of an image of the emission end 190β of the light guide 190b at the center position of the aperture 112a of the aperture mirror 112 (at a position on the optical axis of the imaging optical system 120). The alignment light passed through the aperture 112a of the aperture mirror 112 is projected onto the cornea of the eye E via the objective lens 113.

In a case that a positional relation between the eye E and the retinal camera unit 1A (the objective lens 113) is proper, namely, a distance between the eye E and the retinal camera unit 1A (a working distance) is proper, and the optical axis of the optical system of the retinal camera unit 1A (substantially) coincide with the axis of the eye E (a corneal apex position), two light fluxes formed by the two-hole aperture 190d (alignment light fluxes) are projected onto the eye E so as to be imaged at the intermediate position between the corneal apex and the center of corneal curvature.

The corneal reflection lights of the two alignment light fluxes (alignment lights) are received by the image pick-up element 10a via the imaging optical system 120. An image captured by the imaging device 10a is displayed on a display device such as the touch panel monitor 11 or a display (described later) of the arithmetic and control unit 200. A display pattern of the alignment light in this case is shown in FIGS. 3A and 3B.

Figure 3A:
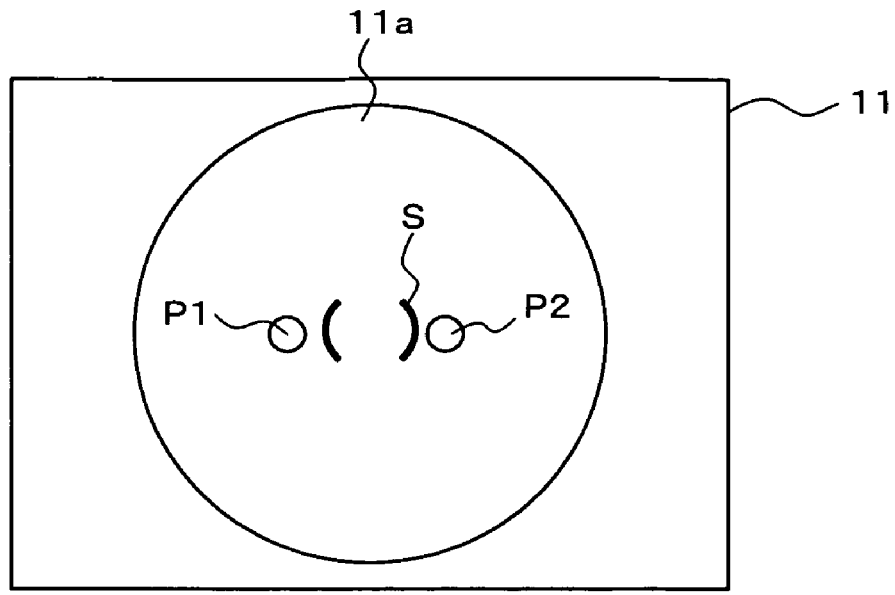
FIGS. 3A and 3B are schematic diagrams for explaining an example of an alignment operation in the preferred embodiment of the fundus oculi observation device according to the present invention.
Figure 3B:
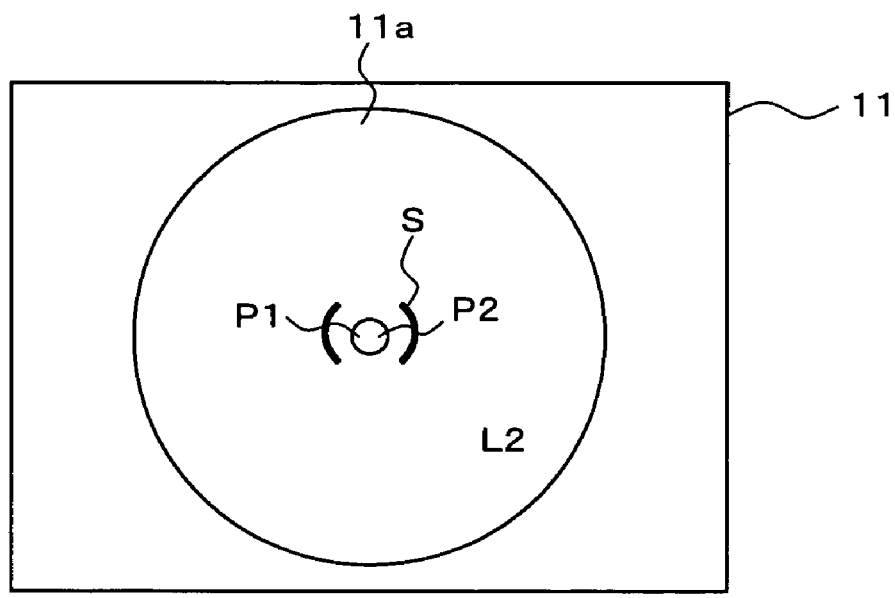

Symbol S in FIGS. 3A and 3B represents a scale having a parenthesis shape, and symbols P1 and P2 represent light-receiving images (alignment bright points) of the two alignment light fluxes. The scale S is displayed on the touch panel monitor 11 so that the center position coincides with the optical axis of the imaging optical system 120.

In a case that the position of the eye E and the position of the retinal camera unit 1A are misaligned in the vertical direction (y-direction) or the horizontal direction (x-direction), the alignment bright points P1 and P2 are displayed in misaligned positions with respect to the scale S in the vertical direction or the horizontal direction as shown in FIG. 3A. In a case that the positions in the xy-directions of the eye E and the retinal camera unit 1A coincide, the alignment bright points P1 and P2 are displayed in the scale S.

In a case that the working distance is not proper, the alignment bright points P1 and P2 are displayed at different positions from each other. In a case that the working distance is proper, the alignment bright points P1 and P2 are displayed in the mutually overlapped state.

In particular, in a case that the positions in the xy-directions of the eye E and the retinal camera unit 1A coincide with each other and the working distance is proper, the alignment bright points P1 and P2 are displayed in the scale S in the mutually overlapped state as shown in FIG. 3B. The examiner executes the alignment by adjusting the positional relation between the eye E and the retinal camera unit 1A so that the alignment bright points P1 and P2 are overlapped with each other and are displayed in the scale S.

The alignment optical system 190A is an example of the "alignment part" of the present invention.

[Configuration of OCT Unit]

Next, the configuration of the OCT unit 150 will be described with reference to FIG. 5.

The OCT unit 150 shown in FIG. 5 is a device for forming a tomographic image of the fundus oculi based on data acquired by optical scan (data detected by the CCD 184 described later). The OCT unit 150 is provided with the substantially same optical system as in a conventional optical image measurement device, namely, an interferometer that splits a light emitted from the light source into a reference light and a signal light and superimposes the reference light propagated through a reference object and the signal light propagated through a measurement object (the fundus oculi Ef) to generate an interference light, and a part configured to detect this interference light and output a signal to the arithmetic and control unit 200. The arithmetic and control unit 200 analyzes this signal and forms an image of the fundus oculi Ef.

A low-coherence light source 160 is composed of a broadband light source, such as a super luminescent diode (SLD) or a light emitting diode (LED), which emits a low-coherence light L0. This low-coherence light L0 is, for example, a broadband light that includes a wavelength of near-infrared region and has a temporal coherence length of approximately several tens of micrometers. The low-coherence light L0 includes a wavelength component included in a longer wavelength than an illumination light of the retinal camera unit 1A (wavelength: about 400-800 nm), for example, a wavelength included in a range of about 800-900 nm.

The low-coherence light L0 emitted from the low-coherence light source 160 is guided to an optical coupler 162 through an optical fiber 161 composed of, for example, a single mode fiber or a PM (polarization maintaining) fiber. The optical coupler 162 splits this low-coherence light L0 into a reference light LR and the signal light LS.

Although the optical coupler 162 acts as both a part for splitting light (a splitter) and a part for superposing lights (a coupler), it will be herein referred to as an "optical coupler" idiomatically.

The reference light LR generated by the optical coupler 162 is guided by an optical fiber 163 composed of a single mode fiber or the like, and emitted from the end face of the fiber. Then, the reference light LR is collimated by a collimator lens 171, propagated through a glass block 172, a density filter 173 and a pair prism 175, and reflected by a reference mirror 174 (a reference object).

The reference light LR reflected by the reference mirror 174 is propagated through the pair prism 175, the density filter 173 and the glass block 172 again, and converged to the fiber end face of the optical fiber 163 by the collimator lens 171. The converged reference light LR is guided to the optical coupler 162 through the optical fiber 163.

The glass block 172 and the density filter 173 act as a delaying part for making the light path lengths (optical distances) of the reference light LR and the signal light LS coincide, and also as a part for making the dispersion characteristics of the reference light LR and the signal light LS coincide.

Further, the reference mirror 174 is configured to be moved in the traveling direction (the directions of the arrow shown in FIG. 5) of the reference light LR. Thus, the light path length of the reference light LR according to the axial length of the eye E or the like is ensured. The reference mirror 174 is moved by a drive mechanism (a reference mirror drive mechanism 243 described later; refer to FIG. 7) including a driver such as a motor.

The pair prism 175 is composed of two prisms. The respective prisms are configured to be movable in the directions orthogonal to the light path of the reference light LR. Each of the prisms is driven to move by a prism drive mechanism 244 shown in FIG. 7. The prism drive mechanism 244 includes an actuator such as a motor that outputs a driving force, a transmission member such as a gear that transmits the driving force, and so on. Such movement of the respective prisms makes the pair prism 175 act so as to change the light path length for each wavelength component of the reference light LR.

The pair prism 175 and the prism drive mechanism 244 configure an example of the "changing part" of the present invention. Further, the prism drive mechanism 244 is an example of the "drive mechanism" of the present invention. Furthermore, the pair prism 175 is an example of the aforementioned dispersion compensation optical element.

The prism drive mechanism 244 is controlled by the main controller 211 described later to move each of the prisms in the direction orthogonal to the light path of the reference light LR, thereby changing the position of each of the prisms on the light path of the reference light LR. Thus, a crossover distance between the light path of the reference light LR and each of the prisms is changed, and the amount of dispersion exerted by the pair prism 175 on the reference light LR is changed.

Further, the prism drive mechanism 244 rotates the pair prism 175 around the center of the light path of the reference light LR, thereby changing the position of each of the prisms on the light path of the reference light LR. Consequently, the direction of dispersion exerted by the pair prism 175 on the reference light LR is changed.

Although the pair prism 175 used in this embodiment is composed of a pair of prisms, the same action may be achieved by using three or more prisms.

Further, the pair prism may be installed on the signal light side. In this case, the light path length for each wavelength component of the signal light is changed.

Further, instead of using a plurality of prisms, it is possible to use a liquid cell. The liquid cell is an optical member which has a housing having a shape for changing the light path length for each wavelength component of light and which contains a liquid sealed in the housing. The liquid cell is, for example, a water cell in which water is sealed.

In a case that the liquid cell is used, a mechanism for changing the amount of liquid sealed in the liquid cell (a change mechanism) is installed as conventional. This change mechanism is controlled by the main controller 211 described later to change the liquid amount. Moreover, this change mechanism rotates the liquid cell around the center of the light path of the reference light LR, thereby changing the direction of dispersion exerted by the liquid cell on the reference light LR.

Other than using a plurality of prisms and a liquid cell, it is possible to apply any optical member that exerts the same action.

The signal light LS generated by the optical coupler 162 is guided to the end of the connection line 152 through an optical fiber 164 composed of a single mode fiber or the like. As described above, the conductive optical fiber 152a runs inside the connection line 152. The optical fiber 164 and the optical fiber 152a may be composed of a single optical fiber, or may be integrally formed by, for example, jointing the end faces of the respective fibers. In either case, it is sufficient as far as the optical fibers 164 and 152a are configured to be capable of transmitting the signal light LS between the retinal camera unit 1A and the OCT unit 150.

The signal light LS is led through the inside of the connection line 152 and guided to the retinal camera unit 1A. Then, the signal light LS enters the eye E through the lens 142, the scan unit 141, the dichroic mirror 134, the imaging lens 126, the relay lens 125, the focusing lens 124, the imaging diaphragm 121, the aperture 112a of the aperture mirror 112 and the objective lens 113 (at this moment, the barrier filters 122 and 123 are retracted from the light path, respectively).

The signal light LS having entered the eye E forms an image on the fundus oculi (retina) Ef and is then reflected. At this moment, the signal light LS is not only reflected on the surface of the fundus oculi Ef but also scattered at the refraction index boundary after reaching the deep area of the fundus oculi Ef. Therefore, the signal light LS propagated through the fundus oculi Ef is a light including information reflecting the surface morphology of the fundus oculi Ef and information reflecting the state of backscatter at the refraction index boundary of the deep area tissue. This light may be simply referred to as "fundus oculi reflection light of the signal light LS."

The fundus oculi reflected light of the signal light LS travels reversely on the above path to be converged at the end face 152b of the optical fiber 152a, enters the OCT unit 150 through the optical fiber 152a, and returns to the optical coupler 162 through the optical fiber 164. The optical coupler 162 superimposes this signal light LS and the reference light LR reflected by the reference mirror 174, thereby generating the interference light LC. The generated interference light LC is guided into a spectrometer 180 through an optical fiber 165 composed of a single mode fiber or the like.

Although a Michelson-type interferometer is employed in this embodiment, it is possible to appropriately employ any type of interferometer.

The spectrometer 180 includes a collimator lens 181, a diffraction grating 182, an image forming lens 183, and a CCD 184. The diffraction grating 182 in the present embodiment is a transmission-type diffraction grating, but a reflection-type diffraction grating can also be used. Moreover, it is needless to say that, instead of the CCD 184, other photodetecting elements can be applied.

The interference light LC having entered the spectrometer 180 is collimated by the collimator lens 181 and thereafter divided into spectra by the diffraction grating 182 (spectral resolution). The interference light LC divided into spectra forms an image on the image pick-up surface of the CCD 184 by the image forming lens 183. The CCD 184 receives the interference light LC to convert into electrical detection signals, and outputs the detection signals to the arithmetic and control unit 200.

[Configuration of Arithmetic and Control Unit]

Next, the configuration of the arithmetic and control unit 200 will be described. The arithmetic and control unit 200 analyzes the detection signals inputted from the CCD 184 of the spectrometer 180 of the OCT unit 150, and forms a tomographic image of the fundus oculi Ef of the eye E. A technique for the analysis is the same as a conventional technique for the Fourier domain OCT.

Further, the arithmetic and control unit 200 forms (image data of) a two-dimensional image showing the morphology of the surface (retina) of the fundus oculi Ef based on the video signals outputted from the imaging devices 10 and 12 of the retinal camera unit 1A.

Furthermore, the arithmetic and control unit 200 executes control of each part of the retinal camera unit 1A and the OCT unit 150.

Control of the retinal camera unit 1A is, for example: control of emission of the illumination light by the observation light source 101 or the imaging light source 103; control of insertion/retraction of the exciter filters 105 and 106 or the barrier filters 122 and 123 to/from the light path; control of display of the LCD 140 or the like; control of movement of the illumination diaphragm 110 (control of the diaphragm value); control of the diaphragm value of the imaging diaphragm 121; control of movement of the focusing lens 124; control of ON/OFF of the alignment light source 190a; and control of the rotation of the Galvano mirrors 141A and 141B within the scan unit 141.

On the other hand, control of the OCT unit 150 is, for example: control of emission of a low-coherence light by the low-coherence light source 160; control of movement of the reference mirror 174; control of movement of each prism of the pair prism 175; and control of an accumulated time of the CCD 184.

An example of the hardware configuration of the arithmetic and control unit 200 that acts as described above will be described with reference to FIG. 6. The arithmetic and control unit 200 is provided with the same hardware configuration as that of a conventional computer. To be specific, the arithmetic and control unit 200 includes: a microprocessor 201 (CPU, MPU or the like), a RAM202, a ROM203, a hard disk drive (HDD) 204, a keyboard 205, a mouse 206, a display 207, an image forming board 208, and a communication interface (I/F) 209. These parts are connected via a bus 200a.

The microprocessor 201 executes operations characteristic to the present embodiment, by loading a control program 204a stored in the hard disk drive 204, onto the RAM 202. The control program 204a is an example of the "program" of the present invention.

Further, the microprocessor 201 executes control of each part of the device described above, various arithmetic processes, and so on. Moreover, the microprocessor 201 executes control of each part of the device corresponding to an operation signal from the keyboard 205 or the mouse 206, control of a display process by the display 207, and control of a transmission/reception process of various data, control signals and so on by the communication interface 209.

The keyboard 205, the mouse 206, and the display 207 function as user interfaces in the fundus oculi observation device 1. The keyboard 205 is used as, for example, a device for typing letters, figures, and so on. The mouse 206 is used as a device for performing various input operations to the display screen of the display 207.

Further, the display 207 is any display device such as an LCD or a CRT (Cathode Ray Tube). The display 207 displays an image of the fundus oculi Ef formed by the fundus oculi observation device 1, and also displays various operation screens and set-up screens.

The user interface of the fundus oculi observation device 1 is not limited to such a configuration, and can be configured by any user interface that is provided with a function of displaying and outputting various information and a function of inputting various information such as a trackball, a joystick, a touch-panel LCD and a control panel for ophthalmic examination.

The image forming board 208 is a dedicated electronic circuit that executes a process of forming (image data of) an image of the fundus oculi Ef of the eye E. The image forming board 208 is provided with a fundus oculi image forming board 208a and an OCT image forming board 208b. The fundus oculi image forming board 208a is a dedicated electronic circuit that operates so as to form image data of a fundus oculi image based on video signals from the imaging device 10 and the imaging device 12 of the retinal camera unit 1A. The OCT image forming board 208b is a dedicated electronic circuit that operates so as to form image data of a tomographic image of the fundus oculi Ef based on detection signals from the CCD 184 of the spectrometer 180 in the OCT unit 150. By installing the image forming board 208, it is possible to increase the processing speed for forming image data of a fundus oculi image and a tomographic image.

The communication interface 209 executes a process of transmitting control signals from the microprocessor 201, to the retinal camera unit 1A or the OCT unit 150. Moreover, the communication interface 209 executes, for example, a process of receiving video signals from the imaging devices 10 and 12 of the retinal camera unit 1A and detection signals from the CCD 184 of the OCT unit 150 and inputting the signals to the image forming board 208. In this case, the communication interface 209 operates so as to input the video signals from the imaging devices 10 and 12, to the fundus oculi image forming board 208a, and input the detection signals from the CCD 184, to the OCT image forming board 208b.

Further, in a case that the arithmetic and control unit 200 is connected to a network such as a LAN (Local Area Network) or the Internet, it is possible to configure the communication interface 209 so as to be capable of data communication via the network, by providing the communication interface 209 with a network adapter like a LAN card or communication equipment like a modem. In this case, it is possible to install a server that stores the control program 204a and also configure the arithmetic and control unit 200 as a client terminal of the server.

[Configuration of Control System]

The configuration of a control system of the fundus oculi observation device 1 will be described with reference to FIGS. 7 and 8.

[Controller]

The control system of the fundus oculi observation device 1 is configured mainly by a controller 210 of the arithmetic and control unit 200. The controller 210 includes the microprocessor 201, the RAM202, the ROM203, the hard disk drive 204 (control program 204a), and the communication interface 209.

The controller 210 is provided with the main controller 211, the storage 212, and the calculation processor 213.

(Main Controller)

The main controller 211 includes the microprocessor 201, and executes the abovementioned control process and so on based on the control program 204a. The main controller 211 specifically controls the alignment light source 190a, the low-coherence light source 160, the reference mirror drive mechanism 243, the prism drive mechanism 244, and so on. The main controller 211, together with the calculation processor 213, functions as an example of the "controller" in the present invention.

Further, the main controller 211 controls to display a two-dimensional image of the surface of the fundus oculi Ef (the fundus oculi image Ef) and a tomographic image of the fundus oculi Ef (or a three-dimensional image based on tomographic images) on the display 240A. These images may be displayed separately or simultaneously.

Further, the main controller 211 controls each part of the device based on a manipulation signal inputted from the manipulation part 240B to execute an operation corresponding to the manipulation content.

(Storage)

The storage 212 stores various information used in a calculation process and a control process. The storage 212 includes a storage device such as a hard disk drive. The storage 212 specifically stores ocular information 212a and device information 212b.

The ocular information 212a is information on the ocular optical system. The ocular information 212a includes axial length information including values of the axial length and refraction index information including values of the refraction index of the eyeball. These values may be actually measured values of the eye E, values of an eyeball model, or clinically obtained statistic values (for example, average values).

The device information 212b is information on the fundus oculi observation device 1. In particular, the device information 212b includes information on the optical system of the fundus oculi observation device 1, such as an optical distance from the optical coupler 162 (a split position of the low-coherence light L0) to the eye E, the amount of dispersion by an optical member on the light path of the signal light LS and the reference light LR, and the amount of dispersion by the air on the light path. Further, the device information 212b also includes an optical distance from the optical coupler 162 to the objective lens 113. The information included in the device information 212b is determined in accordance with the design of the optical system of the fundus oculi observation device 1, which is known information.

The storage 212 is an example of the "storage" of the present invention.

(Calculation Processor)

The calculation processor 213 executes various calculation processes. The calculation processor 213 includes the microprocessor 201 and so on, and executes a calculation process as described later based on the control program 204a.

The calculation processor 213 is provided with an axial length calculator 213a, an error calculator 213b, and a correction amount calculator 213c.

(Axial Length Calculator)

The axial length calculator 213a calculates the axial length of the eye E. An example of the calculation of the axial length will be described below.

The signal light LS and the reference light LR are generated based on the low-coherence light L0, respectively. Therefore, among components included in the interference light LC, a component having the maximum signal strength is a component based on the signal light LS reflected at a position (depth) of the fundus oculi Ef corresponding to the position of the reference mirror 174. That is to say, considering the optical distance from the optical coupler 162, a component of the signal light LS reflected at a depth of the same optical distance as that to the reference mirror 174 forms the component having the maximum strength of the interference light LC.

Before a measurement, alignment is executed by using the alignment optical system 190A. Consequently, the position of the reference mirror 174 is set so that a predetermined depth of the fundus oculi Ef (for example, the fundus oculi surface) corresponds to the position of the reference mirror 174. In this case, among components of the interference light LC, the strength of the component based on the signal light LS reflected on the fundus oculi surface becomes maximum. Moreover, a distance (working distance) between the objective lens 113 and the eye E is determined by the alignment.

Thus, the light path length of the signal light LS is given as the sum of the optical distance from the optical coupler 162 to the objective lens 113, the working distance, and the path length of the signal light LS inside the eye E. When the signal light LS passes on the axis of the eye E, the intraocular path length is an axial length.

Accordingly, considering that the light path length of the signal light LS is equal to the light path length of the reference light LR, the axial length is obtained by subtracting the optical distance from the optical coupler 162 to the objective lens 113 and the working distance, from the light path length of the reference light LR. The calculated value of the axial length is recorded into the ocular information 212a as the axial length information.

Although the alignment error is ignored in the above description, it is possible to obtain a more accurate value of the axial length by considering the alignment error. The alignment error is obtained by, for example, the error calculator 213b.

Further, instead of thus measuring the axial length of the eye, it is also possible to use clinical values or values of an eyeball model (as mentioned above).

The axial length calculator 213a, together with the optical system used for detection of the interference light LC, acts as an example of the "measurement part" of the present invention.

(Error Calculator)

The error calculator 213b obtains an error in the alignment using the alignment optical system 190A. An example of the method for obtaining the alignment error will be described below.

As in the above description of FIG. 3, when the alignment of the working distance is displaced, the alignment bright points P1 and P2 are displayed separately. The interval between the two alignment bright points P1 and P2 corresponds to the displacement of the alignment.

The error calculator 213b analyzes the fundus oculi image Ef in which the alignment bright points P1 and P2 are shown, specifies the positions of the respective alignment bright points P1 and P2, and obtains a relative distance between these positions, thereby obtaining the interval between the alignment bright points P1 and P2.

This interval can be calculated, considering the imaging magnification ratio, based on the number of pixels between the alignment bright points P1 and P2, for example. Moreover, it is also possible to calculate the interval based on the coordinate values of the respective alignment bright points P1 and P2 in the xy-coordinate system.

Further, it is also required to detect the direction of the alignment error, namely, detect whether the working distance is too short or too long. This detection is performed by grasping the increase and decrease of the interval between the alignment bright points P1 and P2 when the device optical system is moved in the z-direction. More specifically, it is possible to determine that an alignment error is caused in a direction to which the interval increases.

Moreover, it is also possible to detect the direction of the alignment error based on the projection direction when only one of the alignment bright points P1 and P2 is projected onto the fundus oculi Ef. When this method is applied, a shielding mechanism that shields one of the holes 190*d*1 and 190*d*2 of the two-hole aperture 190*d* is incorporated into the alignment optical system 190A.

The error calculator 213*b* is an example of the "detector" that detects the alignment error.

(Correction Amount Calculator)

The correction amount calculator 213*c* calculates the correction amount in the dispersion compensation based on the ocular information 212*a* and the alignment error. This calculation is executed in the abovementioned manner.

More specifically, the correction amount calculator 213*c* first multiplies the axial length information le+Δle and the refraction index information ne that are included in the ocular information 212*a* to calculate the optical distance ne·(le+Δle) of the ocular optical system.

Next, the correction amount calculator 213*c* obtains the abovementioned equations (5)-(7) for a plurality of wavelength components of the low-coherence light L0 (for example, the center wavelength, short-wavelength components and long-wavelength components of the half width).

Based on the result of the alignment executed in advance, the reference mirror 174 is placed at a position corresponding to the surface of the fundus oculi Ef. The light path length of the reference light LR (left hand side of these equations) is obtained from the position of the reference mirror 174.

Subsequently, the correction amount calculator 213*c* solves the equations (5)-(7) to calculate the correction distances Ld, Ld1 and Ld2.

Then, based on the correction distances Ld, Ld1 and Ld2, the correction amount calculator 213*c* obtains the correction amount of dispersion, namely, how much each prism of the pair prism 175 should be moved from the standard position.

The correction distance and the movement distance (position) of each prism are correlated in advance, and the correlation information is stored in the storage 212. The correlation is acquired by, for example, measuring the amount of the dispersion correction by the pair prism 175 while changing the position of each prism. Further, it is also possible to theoretically obtain the amount of dispersion correction by the pair prism 175 based on the thickness, refraction index or the like of each prism.

[Image Forming Part]

An image forming part 220 forms image data of a fundus oculi image based on video signals from the imaging devices 10 and 12 of the retinal camera unit 1A. Moreover, the image forming part 220 forms image data of a tomographic image of the fundus oculi Ef based on detection signals from the CCD 184 of the OCT unit 150.

The image forming part 220 includes the image forming board 208, the communication interface 209, and so on. In this specification, "image" may be identified with "image data" corresponding thereto.

[Image Processor]

The image processor 230 executes various image processing on an image formed by the image forming part 220. For example, the image processor 230 forms a three-dimensional image based on a plurality of tomographic images of the fundus oculi Ef. Moreover, the image processor 230 executes various correction processes such as adjustment of luminance of an image.

Image data of a three-dimensional image is image data composed by assigning pixel values to each of a plurality of voxels arranged three-dimensionally. Such image data is referred to as volume data, voxel data, and the like. When displaying an image based on volume data, the image processor 230 executes a rendering process (such as volume rendering and MIP (Maximum Intensity Projection)) on this volume data, and forms image data of a pseudo three-dimensional image seen from a specific viewing direction. On the display 240A, the pseudo three-dimensional image based on the image data is displayed.

[User Interface]

The user interface (UI) 240 is provided with the display 240A composed of a display device such as the display 207, and the manipulation part 240B composed of an input device and a manipulation device such as a keyboard 205 and mouse 206.

A scanning pattern of the signal light LS and a process of forming an OCT image will be described below. The process of forming the fundus oculi image Ef' will not be described because it is the same as conventional.

[Scan with Signal Light]

Scan with the signal light LS is performed by changing the directions of the reflecting surfaces of the Galvano mirrors 141A and 141B of the scan unit 141 in the retinal camera unit 1A. By controlling the mirror drive mechanisms 241 and 242 respectively to change the directions of the reflecting surfaces of the Galvano mirrors 141A and 141B respectively, the main controller 211 scans the fundus oculi Ef with the signal light LS.

When the facing direction of the reflecting surface of the Galvano mirror 141A is changed, scan with the signal light LS is performed in the horizontal direction (x-direction in FIG. 1) on the fundus oculi Ef. On the other hand, when the facing direction of the reflecting surface of the Galvano mirror 141B is changed, scan with the signal light LS is performed in the vertical direction (y-direction in FIG. 1) on the fundus oculi Ef. Further, by changing the facing directions of the reflecting surfaces of both the Galvano mirrors 141A and 141B simultaneously, it is possible to scan with the signal light LS in the composite direction of the x-direction and y-direction. That is, by controlling these two Galvano mirrors 141A and 141B, it is possible to scan with the signal light LS in any direction on the xy plane.

Figure 9A:
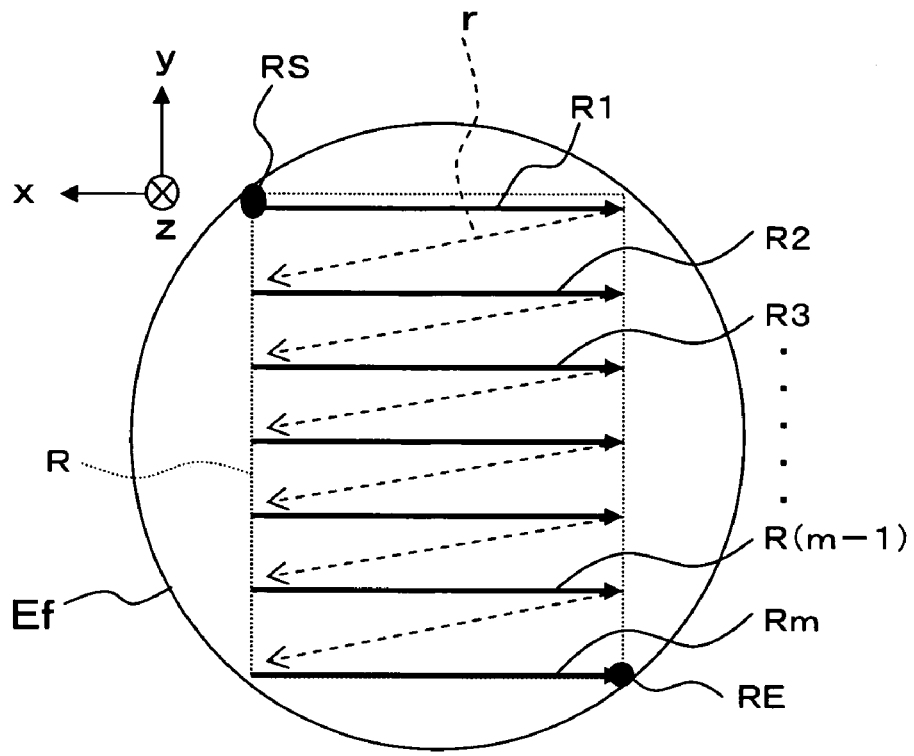
FIGS. 9A and 9B are schematic views showing an example of a scanning pattern of a signal light in the preferred embodiment of the fundus oculi observation device according to the present invention.
Figure 9B:
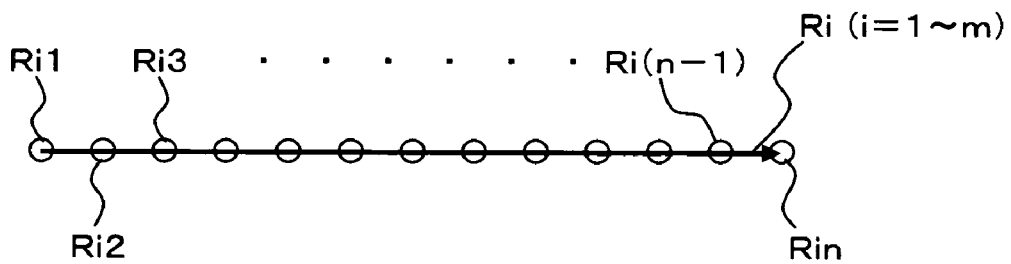

FIGS. 9A and 9B show an example of a scanning pattern of the signal light LS for forming an image of the fundus oculi Ef. FIG. 9A shows an example of a scanning pattern of the signal light LS, when the fundus oculi Ef is seen from a direction that the signal light LS enters the eye E (that is, seen from −z side toward +z side in FIG. 1). Further, FIG. 9B shows an example of an arrangement pattern of scanning points (positions at which image measurement is carried out) on each scanning line on the fundus oculi Ef.

As shown in FIG. 9A, scan with the signal light LS is performed within a rectangular scanning region R set in advance. Within this scanning region R, a plurality of (m lines of) scanning lines R1-Rm are set in the x-direction. When scan with the signal light LS is performed along the respective scanning lines Ri (i=1−m), a detection signal of the interference light LC is generated.

A direction of each scanning line Ri will be referred to as the "main scanning direction" and a direction orthogonal thereto will be referred to as the "sub-scanning direction." Accordingly, a scan with the signal light LS in the main scanning direction is executed by changing the facing direction of the reflecting surface of the Galvano mirror 141A, and scan in the sub-scanning direction is executed by changing the facing direction of the reflecting surface of the Galvano mirror 141B.

On each scanning line Ri, as shown in FIG. 9B, a plurality of (n pieces of) scanning points Ri1-Rin are preset.

In order to execute the scan shown in FIGS. 9A and 9B, the controller 210 firstly controls the Galvano mirrors 141A and 141B to set the incident target of the signal light LS into the fundus oculi Ef to a scan start position RS (scanning point R11) on the first scanning line R1. Subsequently, the controller 210 controls the low-coherence light source 160 to flush the low-coherence light L0, thereby making the signal light LS enter the scan start position RS. The CCD 184 receives the interference light LC based on the fundus oculi reflection light of this signal light LS at the scan start position RS, and outputs the detection signal to the controller 210.

Next, the controller 210 controls the Galvano mirror 141A to scan with the signal light LS in the main scanning direction to set the incident target of the signal light LS to a scanning point R12, and makes the low-coherence light L0 flushed to make the signal light LS enter the scanning point R12. The CCD 184 receives the interference light LC based on the fundus oculi reflection light of this signal light LS at the scanning point R12, and then outputs the detection signal to the controller 210.

Likewise, the controller 210 obtains detection signals outputted from the CCD 184 in response to the interference light LC for each scanning point, by flushing the low-coherence light L0 at each scanning point while sequentially moving the incident target of the signal light LS from a scanning point R13 to R14, - - -, R1($n$–1), and R1$n$.

When the measurement at the last scanning point R1$n$ of the first scanning line R1 is finished, the controller 210 controls the Galvano mirrors 141A and 141B simultaneously to move the incident target of the signal light LS to the first scanning point R21 of the second scanning line R2 following a line switching scan r. Then, by conducting the previously described measurement on each scanning point R2$j$ (j=1–n) of this second scanning line R2, detection signals corresponding to the respective scanning points R2$j$ are obtained.

Likewise, the measurement is conducted for each of the third scanning line R3, - - -, the m–1th scanning line R(m–1), the mth scanning line Rm to acquire the detection signals corresponding to the respective scanning points. Symbol RE on a scanning line Rm is a scan end position corresponding to a scanning point Rmn.

Consequently, the controller 210 acquires m×n pieces of detection signals corresponding to m×n pieces of scanning points Rij (i=1–m, j=1–n) within the scanning region R. Hereinafter, a detection signal corresponding to the scanning point Rij may be represented by Dij.

Such interlocking control of the movement of scanning points and the emission of the low-coherence light L0 can be realized by synchronizing, for instance, timing for transmission of control signals to the mirror drive mechanisms 241 and 242 and timing for transmission of control signals (output request signals) to the low-coherence light source 160.

As described above, when each of the Galvano mirrors 141A and 141B is operated, the controller 210 stores the position of each scanning line Ri and the position of each scanning point Rij (coordinates in the xy coordinate system) as information representing the content of the operation. This stored content (scan position information) is used in an image forming process as conventional.

The scanning pattern of the signal light LS is not limited to the above. For example, it is possible to scan with the signal light LS in any direction, scan along two scanning lines arranged in a cross shape, scan along a plurality of scanning lines arranged radially, scan along a circular scanning line, scan along a plurality of circular scanning lines arranged concentrically, and scan along a spiral scanning line.

[Process of Forming OCT Image]

Next, an example of the processing on an OCT image will be described.

The process of forming a tomographic image by the image forming part 220 includes a two-step arithmetic process as conventional. In the first step of the arithmetic process, based on a detection signal Dij corresponding to each scanning point Rij, a depthwise (z-direction in FIG. 1) image of the fundus oculi Ef at the scanning point Rij is formed.

Figure 10:
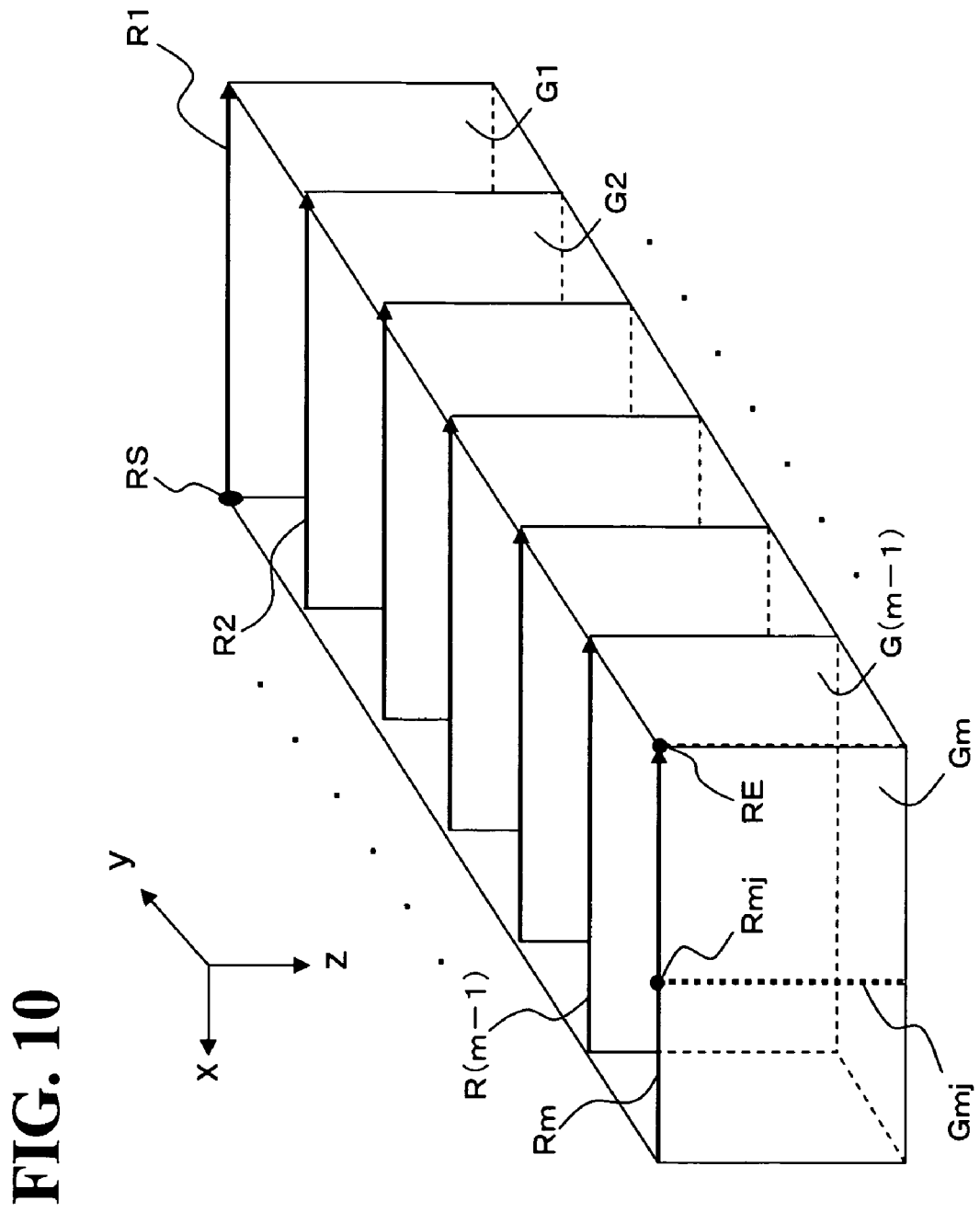
FIG. 10 is a schematic view showing an example of the scanning pattern of the signal light and a pattern of a tomographic image formed along each scanning line in the preferred embodiment of the fundus oculi observation device according to the present invention.

FIG. 10 shows a pattern of tomographic images (group of tomographic images) formed by the image forming part 220. In the second step of the arithmetic process, on each scanning line Ri, based on the depthwise images at the n pieces of scanning points Ri1-Rin, a tomographic image Gi of the fundus oculi Ef along the scanning line Ri is formed. The image forming part 220 is configured to determine the arrangement and interval of the scanning points Ri1-Rin with reference to the positional information (the aforementioned scan position information) of the scanning points Ri1-Rin and form the scanning line Ri. Through the above process, m pieces of tomographic images (group of tomographic images) G1-Gm at different positions in the sub-scanning direction (y-direction) are obtained. The image data of the respective tomographic images G1-Gm are equivalent to image data Ga and so on of the tomographic image shown in FIG. 8 (described later).

Next, a process of forming a three-dimensional image of the fundus oculi Ef by the image processor 230 will be described. A three-dimensional image of the fundus oculi Ef is formed based on the m pieces of tomographic images obtained through the above arithmetic process. The image processor 230 forms a three-dimensional image of the fundus oculi Ef by performing a known interpolating process of interpolating an image between the adjacent tomographic images Gi and G(i+1).

The image processor 230 is configured to determine the arrangement and interval of the scanning lines Ri with reference to the positional information of the scanning lines Ri and form the three-dimensional image. In this three-dimensional image, a three-dimensional coordinate system (x,y,z) is set based on the positional information (the aforementioned scan position information) of the respective scanning points Rij and the z-coordinate in the depth image.

Further, the image processor 230 can form a tomographic image of the fundus oculi Ef at a cross-section in any direction other than the main scanning direction (x-direction), based on this three-dimensional image. When the cross-section is designated, the image processor 230 determines the position of each scanning point on the designated cross-section (and/or an interpolated depthwise image), extracts a depthwise image at each determined position (and/or an interpolated depthwise image), arranges a plurality of extracted depthwise images, thereby forming a tomographic image of the fundus oculi Ef at the designated cross-section.

An image Gmj shown in FIG. 10 represents a depthwise (z-direction) image at the scanning point Rmj on the scanning line Rm. A depthwise image at each scanning point Rij on each scanning line Ri formed in the aforementioned first-step of arithmetic process is represented as an "image Gij."

[Usage Pattern]

Figure 11:
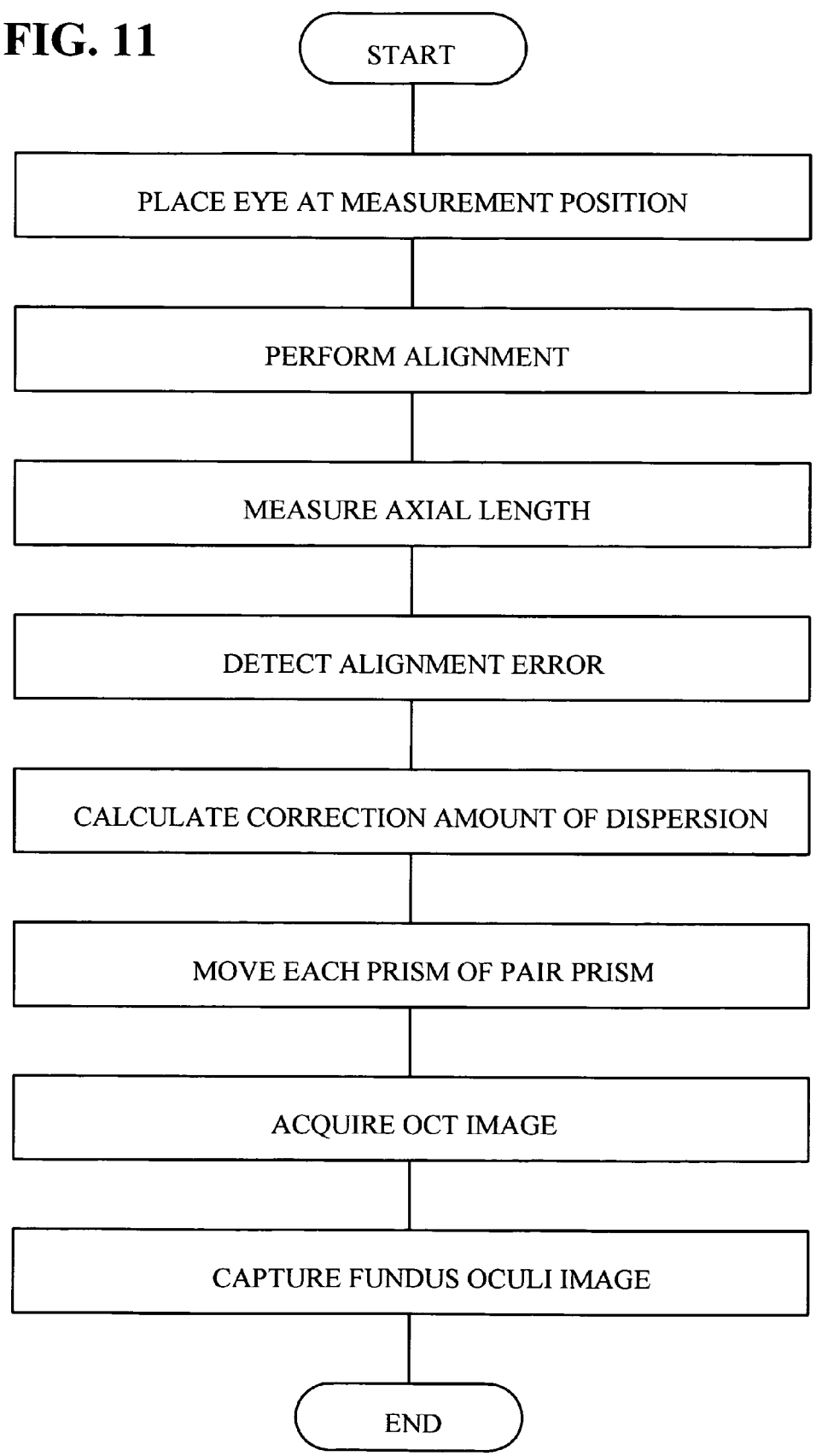
FIG. 11 is a flow chart showing an example of an operation in the preferred embodiment of the fundus oculi observation device according to the present invention.

A usage pattern of the fundus oculi observation device 1 will be described. A flow chart in FIG. 11 shows an example of the usage pattern of the fundus oculi observation device 1.

First, the eye E is placed at a predetermined measurement position (a position facing the objective lens 113) (S1). The fundus oculi observation device 1 is provided with a jaw holder and a forehead support as in a conventional retinal camera to place the eye E so as not to move (not shown).

Next, alignment of the device optical system with the eye E is performed (S2). For this purpose, the operator performs a predetermined manipulation to request start of the alignment. In response to this request, the main controller 211 turns on the alignment light source 190*a* and controls to display the fundus oculi image Ef' on the display 240A. In this fundus oculi image Ef', the alignment bright points P1 and P2 are shown. The operator adjusts the position of the device optical system (the housing of the fundus oculi observation device 1) by, for example, manipulating a lever (not shown), thereby performing the alignment in the x-, y- and z-directions with the eye E.

Next, the axial length is measured (S3). For this purpose, the operator performs a predetermined manipulation to request start of a measurement of the axial length. In response to this request, the main controller 211 places the reference mirror 174 at a position corresponding to the surface of the fundus oculi Ef in the aligned state, and turns on the low-coherence light source 160. The CCD 184 detects the interference light LC generated thereby, and outputs a detection signal. The axial length calculator 213*a* obtains an axial length based on this detection signal in the abovementioned manner. The main controller 211 stores the measurement value of this axial length as the ocular information 212*a*.

Next, an alignment error is detected (S4). This process is performed in consideration that the eye E might move after execution of the alignment. For this purpose, the main controller 211 controls to turn on the alignment light source 190*a* when the axial length measurement is completed and acquire the fundus oculi image Ef' in which the alignment bright points P1 and P2 are shown. The error calculator 213*b* analyzes this fundus oculi image Ef' to obtain the alignment error.

Subsequently, the correction amount calculator 213*c* calculates the dispersion correction amount in the abovementioned manner based on the ocular information 212*a*, the device information 212*b*, the alignment error, and so on. (S5).

The main controller 211 controls the prism drive mechanism 244 based on the result of the calculation of the correction amount to move each prism of the pair prism 175 (S6). Consequently, the pair prism 175 exerts dispersion by the correction amount on the reference light LR. Moreover, the prism drive mechanism 244 rotates the pair prism 175 to change the direction of dispersion to be exerted.

Next, an OCT image of the fundus oculi Ef is acquired (S7). For this purpose, the main controller 211 controls the low-coherence light source 160 and the mirror drive mechanisms 241 and 242 to scan with the signal light LS. The CCD 184 detects the interference light LC based on the fundus oculi reflected light of the signal light LS at each scanning point, and outputs the detection signal. The image forming part 220 forms tomographic images of the fundus oculi Ef based on the sequentially inputted detection signals. When needed, the image processor 230 forms a three-dimensional image and also executes a correction process. The main controller 211 controls to display the OCT images on the display 240A and also store the OCT images into the storage 212.

Finally, the fundus oculi image Ef' is captured (S8). For this purpose, in response to completion of acquisition of OCT images, the main controller 211 controls the observation light source 101 or the imaging light source 103 to turn on and executes capture of the fundus oculi image Ef'. The main controller 211 controls to display the captured fundus oculi image Ef' on the display 240A and also store the image into the storage 212. This usage pattern is thus completed.

[Action and Effect]

The action and effect of the fundus oculi observation device 1 will be described.

As described above, the fundus oculi observation device 1 acts to correct the influence of dispersion of the reference light LR based on the ocular information 212*a*, generate the interference light LC based on the low-coherence light L0 after the correction, detect this interference light LC, and form an OCT image of the fundus oculi Ef based on the result of the detection.

According to the fundus oculi observation device 1, it is possible to perform effective dispersion compensation considering the influence of dispersion by the ocular optical system.

Further, according to the fundus oculi observation device 1, it is possible to perform dispersion compensation in consideration of an alignment error, and therefore, it is possible to perform highly accurate and effective dispersion compensation.

Further, according to the fundus oculi observation device 1, it is possible to measure the axial length of the eye E and perform dispersion compensation based on the measurement result, and therefore, it is possible to highly accurate and effective dispersion compensation for every eye. Moreover, there is such an advantage that it is possible to effectively perform dispersion compensation for an eye in which the axial length has not been measured in advance.

The controller 210, the pair prism 175, and the prism drive mechanism 244 function as an example of the "corrector" of the present invention.

[Modification]

The configuration described above is merely an example for favorably implementing the fundus oculi observation device relating to the present invention. Therefore, it is possible to properly apply any modification within the scope of the present invention.

For example, although the influence of dispersion on the reference light is corrected in the above embodiment, it is also possible to correct the influence of dispersion on the signal light. In this case, the pair prism or the liquid cell is placed on the light path of the signal light. Moreover, the influence of dispersion on both the reference light and the signal light may be corrected. In this case, the pair prism or the like is placed on each of the light paths.

Although an alignment error is acquired before acquisition of an OCT image in the above embodiment, the alignment may be performed again. However, in order to avoid that an examination is prolonged, it seems to be desirable to obtain an alignment error as in the above embodiment.

Further, it is also possible to, when acquiring an OCT image, display an auxiliary index based on an alignment error and make the operator recognize the amount and direction of the alignment error. Further, alignment may be performed automatically based on an alignment error. This automatic alignment can be realized by installing a drive mechanism for moving the device optical system with respect to the eye and controlling the drive mechanism in accordance with the alignment error.

Although the difference in light path length between the light path of the signal light LS and the light path of the reference light LR is changed by changing the position of the reference mirror 174 in the above embodiment, the method for changing the light path length difference is not limited to this method. For example, it is possible to change the light path length difference by integrally moving the retinal camera unit 1A and the OCT unit 150 with respect to the eye E and changing the light path length of the signal light LS. Further, it is also possible to change the light path length difference by moving the measurement object in the depth direction (z-direction).

The fundus oculi observation device described in the above embodiment includes a Fourier-domain type of optical image measurement device. However, it is possible to apply the same configuration to any type of optical image measurement device such as a Swept Source type or a Time Domain type.

Although dispersion is optically corrected in the above embodiment, the influence of dispersion may be corrected by executing image processing on an OCT image. Moreover, it is also possible to complimentarily execute the optical dispersion compensation and the correction by image processing.

The controller 210 may be configured to be capable of executing a correction process as described below, in addition to the correction process described in the above embodiment, namely, the correction process based on the ocular information 212a. This correction process is for correcting the influence of dispersion so as to decrease the value of the depth resolution of an image of the fundus oculi Ef based on a signal outputted from the CCD 184 having detected the interference light LC (the abovementioned detection signal). The detection signal obtained by the CCD 184 is a signal representing the intensity of each wavelength component (each frequency component) included in the interference light LC. Part of the process described below is executed by the image forming part 220.

First, the envelope curve of the detection signals obtained by the CCD 184 is obtained. Next, the controller 210 moves the pair prism 175 so as to widen the width of this envelope curve (the signal width at the wavelength axis or the frequency axis). In this case, it is possible to correct the influence of dispersion so as to widen the width of the envelope curve by detecting the interference light LC sequentially while moving the pair prism 175 and monitoring the width of the envelope curve of the detection signals. The controller 210 may be configured to calculate the position of the pair prism 175 where the width of the envelope curve is widened, based on the detection signals, and move the pair prism 175 based on the result of the calculation. It is desirable to move the pair prism 175 to a position where the width of the envelope curve becomes the widest.

By thus correcting the influence of dispersion so as to widen the width of the envelop curve of the detection signals of the interference light LC, it is possible to decrease the value of the depth resolution of the tomographic image Gi of the fundus oculi Ef as known in the field of Fourier domain OCT. Consequently, it is possible to effectively perform dispersion compensation.

Another correction process will be described. In the imaging process of the Fourier domain OCT, by obtaining a profile in the depth direction by Fourier transform of the detection signals obtained by the CCD 184, and imaging this profile, an image of the fundus oculi Ef is obtained. In this modification, the influence of dispersion is corrected based on signals obtained by Fourier transform of the detection signals (the profile in the depth direction). For this purpose, the controller 210 obtains the half width of the profile in the depth direction and moves the pair prism 175 so as to decrease the half width. In this case, by detecting the interference light LC sequentially while moving the pair prism 175, and monitoring the half width of the signals obtained by Fourier transform of the detection signals, it is possible to correct the influence of dispersion so as to decrease the half width. Alternatively, the controller 210 may be configured to, based on the signals obtained by Fourier transform of the detection signals, calculate the position of the pair prism 175 where the half width decreases and move the pair prism 175 based on the calculation result. It is desirable to move the pair prism 175 to a position where the half width becomes the narrowest.

By thus correcting the influence of dispersion so as to decrease the half width of the signals obtained by Fourier transform of the detection signals of the interference light LC, it is possible to decrease the value of the depth resolution of the tomographic image Gi of the fundus oculi Ef as known in the field of Fourier domain OCT. Consequently, it is possible to effectively perform dispersion compensation.

By performing the correction process for decreasing the value of the depth resolution after the correction process based on the ocular information 212a, it is possible to perform more precise dispersion compensation. Alternatively, in order to evaluate the precision and accuracy of the correction process based on the ocular information 212a, it is also possible to apply the correction process for decreasing the value of the depth resolution.

Further, it is also possible, without performing the correction process based on the ocular information 212a, to apply a fundus oculi observation device that executes the correction process for decreasing the value of the depth resolution. The fundus oculi observation device has the configuration as described below.

First, as in the above embodiment, this fundus oculi observation device splits a broadband light into a signal light and a reference light, superimposes the signal light propagated through the fundus oculi and the reference light propagated through a reference object to generate an interference light, and forms an image of the fundus oculi based on the result of detection of this interference light. Furthermore, this fundus oculi observation device is provided with a corrector that corrects the influence of dispersion so as to decrease the value of the depth resolution of the fundus oculi image based on signals as the result of the detection of the interference light, generates an interference light based on the broadband light after correction, detects this interference light, and forms an image of the fundus oculi of the eye based on the detection result.

According to the fundus oculi observation device, it is possible to correct the influence of dispersion so as to minimize the value of the depth resolution of the image based on the result of detection of the interference light, and form an image of the fundus oculi of the eye based on the result of detection of the interference light generated after the correction, and therefore, it is possible to effectively perform dispersion compensation.

[Program]

A program according to the present invention will now be described. The control program 204a in the above embodiment is an example of the program according to the present invention.

The program according to the present invention is a program that controls a fundus oculi observation device that includes a computer, splits a broadband light into a signal light and a reference light, superimposes the signal light propagated through the fundus oculi and the reference light propagated through a reference object to generate an interference light, and forms an image of the fundus oculi based on the result of detection of the interference light. The computer in the above embodiment is the arithmetic and control unit 200.

This program causes the computer to store ocular information including axial length information and to correct the influence of dispersion of the signal light and/or the reference light based on the ocular information. Furthermore, this program controls the fundus oculi observation device after the correction, generates an interference light based on the broadband light, detects this interference light, and forms an image of the fundus oculi of the eye based on the result of the detection.

According to the program, it is possible to perform effective dispersion compensation considering the influence of dispersion by the ocular optical system.

Further, the program according to the present invention is a program that controls a similar fundus oculi observation device, and causes the computer to correct the influence of dispersion so as to decrease the value of the depth resolution of an image of the fundus oculi based on signals as the result of detection of the interference light. After the correction, the fundus oculi observation device generates an interference light based on the broadband light, detects this interference light, and forms an image of the fundus oculi of the eye based on these detection results.

According to the program, it is possible to effectively perform dispersion compensation.

The program according to the present invention can be stored into an arbitrary storage medium that can be read by a driver of the computer. For example, it is possible to use a storage medium such as an optical disc, a magneto-optical disk (CD-ROM/DVD-RAM/DVD-ROM/MO, or the like), a magnetic storage medium (hard Disk/Floppy™ disk/ZIP drive, or the like). Moreover, it is possible to store into a storage device such as a hard disk drives and a memory. Additionally, this program can also be transmitted through a network such as the Internet or a LAN.

The invention claimed is:

1. A fundus oculi observation device that splits light from a light source into a signal light and a reference light, superimposes the signal light propagated through a fundus oculi and the reference light propagated through a reference object to generate an interference light, and forms an image of the fundus oculi based on a result of detection of the interference light, the fundus oculi observation device comprising:
a storage configured to store ocular information including axial length information; and
an optical element for dispersion compensation placed on the light path of the reference light; and
a corrector configured to obtain a correction amount of the optical element to correct an influence of dispersion exerted on the signal light and/or the reference light, based on the ocular information, so as to correct a position of the optical element based on the obtained correction amount,
wherein an interference light based on the light from the light source is generated after the correction, the inference light is detected, and an image of the fundus oculi of the eye is formed based on a result of the detection,
wherein the corrector is configured to obtain an equation between a light path length of the signal light and a light path length of the reference light based on the ocular information, and to correct the influence of dispersion based on the equation, and
wherein the ocular information includes refraction index information of an ocular optical system; and the corrector is configured to calculate the light path length of the signal light based on the axial length information, the refraction index information and a light path length from a split position of the light of the light source to the eye, and to obtain an equation of the calculated light path length of the signal light and the light path length of the reference light, as the equation.

2. The fundus oculi observation device according to claim 1, wherein the corrector includes a changing part configured to change a light path length of each wavelength component of the signal light and/or a light path length of each wavelength component of the reference light, and a controller configured to control the changing part based on the ocular information.

3. The fundus oculi observation device according to claim 2, wherein:
the changing part includes a plurality of prisms, and a drive mechanism configured to move each of the plurality of prisms; and
a controller is configured to control the drive mechanism based on the ocular information to change a position of each of the plurality of prisms on a light path of the signal light and/or on a light path of the reference light.

4. The fundus oculi observation device according to claim 2, wherein:
the changing part includes a liquid cell in which a liquid is sealed, and a change mechanism configured to change an amount of the liquid sealed in the liquid cell; and
the controller is configured to control the liquid amount change mechanism based on the ocular information to change a crossover distance between a light path of the signal light and/or a light path of the reference light and the liquid cell.

5. The fundus oculi observation device according to claim 1, wherein the corrector is configured to calculate an optical distance of the ocular optical system based on the axial length information and the refraction index information, to obtain, as the equation, an equation that relates the light path length from the split position to the eye, the light path length of the reference light, the optical distance of the ocular optical system, and an unknown correction distance, for each of a plurality of wavelength components of the broadband light, to calculate the correction distance based on the equation, and to correct the influence of dispersion based on a result of the calculation.

6. The fundus oculi observation device according to claim 1, further comprising an alignment part for performing alignment of a device optical system with the eye, wherein the corrector is configured to calculate the light path length from the split position to the eye based on a result of the alignment.

7. The fundus oculi observation device according to claim 6, wherein the corrector includes a detector configured to detect an error of the alignment, and is configured to obtain the relation expression by reflecting the error.

8. The fundus oculi observation device according to claim 1, wherein the corrector is configured to obtain the light path length of the reference light based on a light path length from a split position of the broadband light to the reference object.

9. The fundus oculi observation device according to claim 1, wherein the corrector includes a changing part configured to change a light path length for each wavelength component of the signal light and/or a light path length for each wavelength component of the reference light, and a controller configured to control the changing part based on the equation.

10. The fundus oculi observation device according to claim 1, further comprising a measurement part configured to measure an axial length of the eye, wherein the storage is configured to store a result of the measurement as the axial length information.

11. The fundus oculi observation device according to claim 1, wherein the corrector is configured to, after correcting the influence of dispersion based on the ocular information, further correct the influence of dispersion so as to decrease the value of a depth resolution of the image of the fundus oculi based on a signal as the result of the detection of the interference light.

12. The fundus oculi observation device according to claim 11, wherein the corrector is configured to correct the influence of dispersion so as to decrease a half width of a signal obtained by Fourier transform of the signal.

13. A fundus oculi observation device that splits light from a light source into a signal light and a reference light, superimposes the signal light propagated through a fundus oculi and the reference light propagated through a reference object to generate an interference light, and forms an image of the fundus oculi based on a result of detection of the interference light, the fundus oculi observation device comprising:
- a storage configured to store ocular information including axial length information; and
- an optical element for dispersion compensation placed on the light path of the reference light; and
- a corrector configured to obtain a correction amount of the optical element to correct an influence of dispersion exerted on the signal light and/or the reference light, based on the ocular information, so as to correct a position of the optical element based on the obtained correction amount, wherein an interference light based on the light from the light source is generated after the correction, the inference light is detected, and an image of the fundus oculi of the eye is formed based on a result of the detection, wherein the corrector is configured to, after correcting the influence of dispersion based on the ocular information, further correct the influence of dispersion so as to decrease the value of a depth resolution of the image of the fundus oculi based on a signal as the result of the detection of the interference light, and wherein the corrector is configured to correct the influence of dispersion so as to widen a width of an envelope curve of the signal.

14. A program stored on a non-transitory computer readable medium that controls a fundus oculi observation device including a computer, the program controlling the fundus oculi observation device to:
- splits a light from a light source into a signal light and a reference light,
- superimposes the signal light propagated through a fundus oculi and the reference light propagated through a reference object to generate an interference light, and
- forms an image of the fundus oculi based on a result of detection of the interference light, wherein:
- the fundus oculi observation device includes:
- an optical element for dispersion compensation placed on the light path of the reference light; and,
- the computer is caused to store ocular information including axial length information and obtain a correction amount of the optical element placed on the light path of the reference light to correct an influence of dispersion exerted on the signal light and/or the reference light based on the axial length information, so as to correct the position of the optical element based on the obtained correction amount; and the fundus oculi observation device, after the correction, generates an interference light based on the light from the light source, detects the interference light, and forms an image of the fundus oculi of the eye based on a result of the detection.

15. A program stored on a non-transitory computer readable medium that controls a fundus oculi observation device including a computer, the program controlling the fundus oculi observation device to:
- splits a light from a light source into a signal light and a reference light,
- superimposes the signal light propagated through a fundus oculi and the reference light propagated through a reference object to generate an interference light, and
- forms an image of the fundus oculi based on a result of detection of the interference light, wherein:
- the fundus oculi observation device includes:
- an optical element for dispersion compensation placed on the light path of the reference light; and,
- the computer is caused to obtain a correction amount of the optical element placed on the light path of the reference light to correct the influence of dispersion so as to decrease the value of a depth resolution of the image of the fundus oculi, based on a signal as the result of the detection of the interference light, so as to correct the position of the optical element based on the obtained correction amount; and
- the fundus oculi observation device, after the correction, generates an interference light based on the light from the light source, detects the interference light, and forms an image of the fundus oculi of the eye based on a result of the detection.

16. A fundus oculi observation device that splits light from a light source into a signal light and a reference light, superimposes the signal light propagated through a fundus oculi and the reference light propagated through a reference object to generate an interference light, and forms an image of the fundus oculi based on a result of detection of the interference light, the fundus oculi observation device comprising:
- an optical element for dispersion compensation placed on the light path of the reference light; and
- a corrector configured to obtain a correction amount of the optical element to correct an influence of dispersion so as to decrease the value of a depth resolution of the image of the fundus oculi, based on a signal as a result of detection of the interference light, so as to correct a position of the optical element based on the obtained correction amount, wherein an interference light based on the light from the light source is generated after the correction, the inference light is detected, and an image of the fundus oculi of the eye is formed based on a result of the detection, and wherein the corrector is configured to correct the influence of dispersion so as to widen a width of an envelope curve of the signal.

* * * * *